(12) United States Patent
Zhou

(10) Patent No.: US 10,952,999 B2
(45) Date of Patent: Mar. 23, 2021

(54) INHIBITOR OF CYCLIN-DEPENDENT KINASE CDK9

(71) Applicant: GENFLEET THERAPEUTICS (SHANGHAI) INC., Shanghai (CN)

(72) Inventor: Gang Zhou, Shanghai (CN)

(73) Assignee: GENFLEET THERAPEUTICS (SHANGHAI) INC., Shanghai (CN)

( * ) Notice: Subject to any disclaimer, the term of this patent is extended or adjusted under 35 U.S.C. 154(b) by 0 days.

(21) Appl. No.: 16/606,136

(22) PCT Filed: Jan. 3, 2018

(86) PCT No.: PCT/CN2018/070108
§ 371 (c)(1),
(2) Date: Nov. 14, 2019

(87) PCT Pub. No.: WO2018/192273
PCT Pub. Date: Oct. 25, 2018

(65) Prior Publication Data
US 2020/0078343 A1    Mar. 12, 2020

(30) Foreign Application Priority Data
Apr. 19, 2017 (CN) .......................... 201710257652.7

(51) Int. Cl.
| | | |
|---|---|---|
| *A61K 31/443* | (2006.01) | |
| *A61K 45/06* | (2006.01) | |
| *A61P 35/00* | (2006.01) | |
| *A61P 35/02* | (2006.01) | |
| *C07D 417/04* | (2006.01) | |
| *C07D 417/14* | (2006.01) | |
| *A61K 31/4439* | (2006.01) | |

(52) U.S. Cl.
CPC .......... *A61K 31/4439* (2013.01); *A61K 45/06* (2013.01); *A61P 35/00* (2018.01); *C07D 417/04* (2013.01); *C07D 417/14* (2013.01)

(58) Field of Classification Search
CPC .. A61K 31/4439; A61K 45/06; A61K 31/427; A61P 35/00; A61P 35/02; C07D 417/04; C07D 417/14
See application file for complete search history.

(56) References Cited

FOREIGN PATENT DOCUMENTS

| | | |
|---|---|---|
| CN | 101472920 A | 7/2009 |
| CN | 10333994 A | 10/2013 |
| CN | 1505626 A | 6/2014 |
| WO | 2009118567 A2 | 10/2009 |
| WO | 2012101062 A1 | 8/2012 |
| WO | 2013156780 A1 | 10/2013 |
| WO | 2018192273 A1 | 10/2018 |

OTHER PUBLICATIONS

International Search Report for related International Application No. PCT/CN2018/070108, dated Apr. 11, 2018, 2 pages.
Green et al., "Design, Synthesis, and Structure-Activity Relationships of Pyridine-based Rho Kinase (ROCK) Inhibitors", Article, Journal of Medicinal Chemistry, vol. 58, Jun. 3, 2015, pp. 5028-5037.
Office Action for the related Chinese Patent Application No. 201710257652.7 dated Jan. 6, 2020, 7 pages.
Green et al., "Design, Synthesis, and Structure-Activity Relationships of Pyridine-based Rho Kinase (ROCK) Inhibitors", Journal of Medicinal Chemistry, published at American Chemical Society, dated Jun. 3, 2015, 10 pages.
Office Action for the related European Patent Application No. 18787869.9-1110/3613737 dated Jul. 23, 2020, 8 pages.

*Primary Examiner* — John M Mauro
(74) *Attorney, Agent, or Firm* — Ditthavong & Steiner P. C.

(57) ABSTRACT

The present invention relates to an inhibitor of cyclin-dependent kinase CDK9, having a structure of formula (I). The present invention also provides a method of treating a cancer or a precancerous condition related to CDK9 activity with the inhibitor and a use of the same.

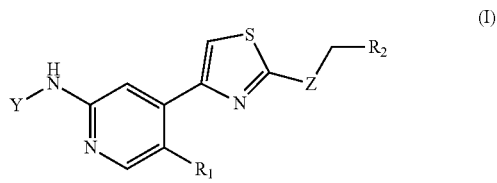

10 Claims, 9 Drawing Sheets

INHIBITOR OF CYCLIN-DEPENDENT KINASE CDK9

CROSS-REFERENCES TO RELATED APPLICATIONS

This application claims priority from PCT Application Serial No. PCT/CN2018/070108, entitled "Novel inhibitor of cyclin-dependent kinase CDK9," filed on Jan. 3, 2018, which claims priority from Chinese Application Serial No. CN201710257652.7 filed Apr. 19, 2017, the contents of which are hereby incorporated herein in their entirety by this reference.

TECHNICAL FIELD

The present application relates to compounds which act as cyclin-dependent kinase CDK9 inhibitors, pharmaceutical compositions comprising these compounds, and methods and uses for inhibiting serine kinase activity using these compounds or compositions.

BACKGROUND

Proliferation and division of eukaryotic cells is an accurate and complex regulatory process. The process of proliferation is accomplished through cell cycle, and the orderly progression of the cell cycle is through its strict molecular regulatory mechanisms. It has been found that there are three major classes of molecules involved in cell cycle regulation: cyclin-dependent kinases (CDK), cyclins, and cyclin-dependent kinase inhibitors. CKI), among them, CDK is at the center. 13 members (CDK1-CDK13) of CDK family have been found, which are classified into two categories according to their intracellular functions: CDK that controls the cell cycle and CDK that controls cell transcription. CDK9 belongs to serine kinase, and its complex formed with the corresponding cyclin is called positive transcription elongation factor b (P-TEFb). The complex can phosphorylate RNA polymerase II and some negative transcription elongation factors (NELF and N-TEF) allowing transcription to be extended from the initiation site and is core molecule for transcriptional elongation (Sims R J $3^{rd}$ et al., Genes Dev, 2004, 18: 2437-68; Yamaguchi Y et al., Mol Cell Biol, 2002, 22: 2918-27). Studies have found that abnormal expression levels of CDK9 or (and) abnormal kinase activity will cause abnormal expression of various proteins or (and) its abnormal mRNA levels in the cell. Among them, anti-apoptotic proteins, such as Bcl-2, cell cycle-associated regulatory proteins, such as cyclin D1, p53 pathway-related proteins, certain proteins of the NF-κB pathway, and proteins related to the tumor microenvironment, such as VEGF and the like have been confirmed to be closely related to tumors. It can be said that CDK9 is one of the most critical molecules in the development of tumors (Shapiro GI. J Clin Oncol, 2006, 24: 1770-83).

SUMMARY OF THE INVENTION

The invention relates to inhibitors of cyclin dependent kinases. In particular, in the present invention there is provided a compound of formula (I), or a pharmaceutically acceptable salt, solvate, ester, acid, metabolite or prodrug thereof:

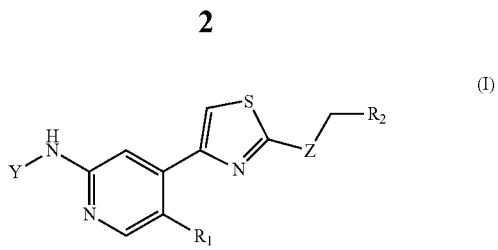

wherein Y is selected from the group consisting of p-fluorobenzoyl, trans-4-aminocyclohexyl in which N is optionally substituted with $R_3$, and trans-4-aminocyclohexylmethyl in which N is optionally substituted with $R_3$;

Z is selected from the group consisting of NH, S and O;

$R_1$ is selected from the group consisting of hydrogen and halogen;

$R_2$ is selected from the group consisting of hydrogen, C1-C3 alkyl, C3-C6 cycloalkyl, C3-C6 heterocycloalkyl optionally substituted with $R_4$, and phenyl optionally substituted with $R_4$;

$R_3$ is selected from the group consisting of C2-C6 alkanoyl and C1-C3 alkoxy (C1-C3) alkyl;

$R_4$ is selected from the group consisting of cyano and halogen.

In the present invention there is also provided a pharmaceutical composition comprising a compound of formula (I), or a pharmaceutically acceptable salt, solvate, ester, acid, metabolite or prodrug thereof, and a pharmaceutically acceptable carrier or excipient and optionally other therapeutic agents.

The present invention further relates to a use of a compound of formula (I), or a pharmaceutically acceptable salt, solvate, ester, acid, metabolite or prodrug thereof in the preparation of a drug for the treatment, prevention or amelioration of a disease, disorder or condition regulated or effected by serine kinase activity or related to cyclin-dependent kinase activity. Among them, the disease, disorder or condition is preferably cancer.

FIGURES

Figure 4A:
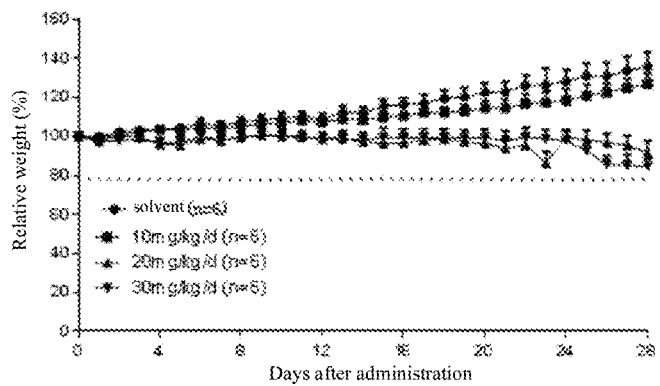
Figure 4B:
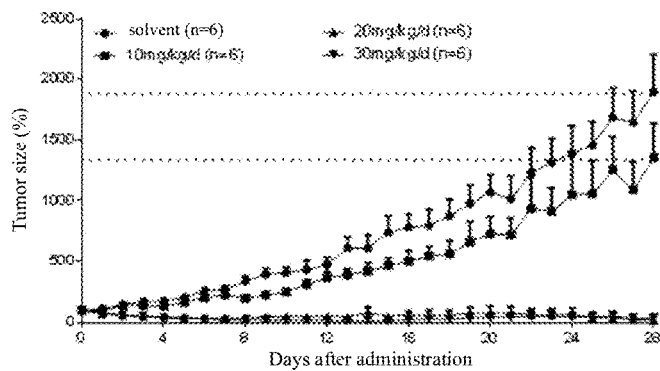
Figure 4C:
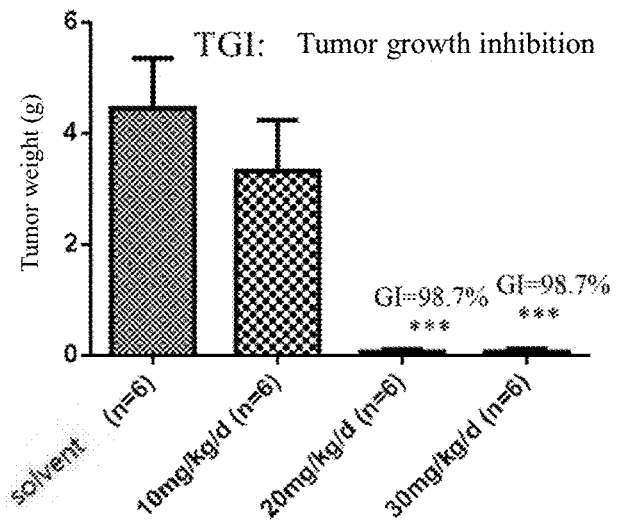

FIGS. 4a-4c show the results of an experiment in which compound 1 inhibits tumor growth in a tumor mouse model, wherein FIG. 4a shows a change in the relative body weight of the mice subcutaneously injected with leukemia cells (calculated based on the body weight on the first day of administration) over time; FIG. 4b shows the change in the mouse-loaded tumor size over time; FIG. 4c shows the finally calculated tumor inhibition rate (TGI) for each group, and the values for each data point shown in the figures reflect the mean of each experimental group.

DETAILED DESCRIPTION OF THE INVENTION

Term

Unless otherwise defined, all technical and scientific terms used herein have the same meaning as commonly understood by one of ordinary skill in the art to which the claimed subject matter pertains.

Unless otherwise indicated, conventional methods such as mass spectrometry, NMR, HPLC, protein chemistry, biochemistry, recombinant DNA techniques, and pharmacology within the skill of the art are used in the present invention. Unless a specific definition is provided, nomenclature and laboratory operations and techniques chemically related to analytical chemistry, synthetic organic chemistry, and medical and pharmaceutical chemistry described herein are known to those skilled in the art. In general, the foregoing techniques and procedures can be carried out by conventional methods well known in the art and described in various general and more specific documents, which are cited and discussed in this specification.

"Alkyl" refers to an aliphatic hydrocarbon group which may be a branched or straight alkyl. Depending on the structure, an alkyl group may be a monovalent group or a divalent group (i.e., an alkylene group). In the present invention, the alkyl group is preferably a "lower alkyl group" having 1 to 6 carbon atoms, and even more preferably a "lower alkyl group" having 1 to 3 carbon atoms. Typical alkyl groups include, but are not limited to, methyl, ethyl, propyl, isopropyl, butyl, isobutyl, tert-butyl, pentyl, hexyl, and the like.

"Alkoxy" refers to an —O-alkyl group wherein alkyl is as defined herein. Typical alkoxy groups include, but are not limited to, methoxy, ethoxy, propoxy, butoxy, pentyloxy, hexyloxy, and the like.

The term "aryl" means that the planar ring has a delocalized ρ-electron system and contains 4n+2ρ electrons, where n is an integer. The aryl ring may be composed of five, six, seven, eight, nine or more than nine atoms. The aryl group can be optionally substituted. The term "aryl" includes carbocyclic aryl groups (such as phenyl) and heterocyclic aryl (or "heteroaryl" or "hetero aromatic") groups (such as pyridine). The term includes monocyclic or fused polycyclic (ie, rings that share adjacent pairs of carbon atoms) groups.

The term "aryl" as used herein means that each of the atoms constituting the ring in the aryl ring is a carbon atom. The aryl ring may be composed of five, six, seven, eight, nine or more than nine atoms. The aryl group can be optionally substituted. Examples of aryl groups include, but are not limited to, phenyl, naphthyl, phenanthryl, anthryl, fluorenyl, and fluorenyl. Depending on the structure, an aryl group may be a monovalent group or a divalent group (i.e., an arylene group).

"Alkyl (aryl)" refers to an alkyl group, as defined herein, substituted with an aryl group, as defined herein. Non-limiting alkyl (aryl) groups include benzyl, phenethyl and the like.

The term "cycloalkyl" refers to a monocyclic or polycyclic group containing only carbon and hydrogen. The cycloalkyl group includes a group having 3 to 10 ring atoms. Depending on the structure, a cycloalkyl group may be a monovalent group or a divalent group (i.e., a cycloalkylene group). In the present invention, the cycloalkyl group is preferably a cycloalkyl group having 3 to 8 carbon atoms, and even more preferably a "lower cycloalkyl group" having 3 to 6 carbon atoms.

"Alkyl (cycloalkyl)" refers to an alkyl group, as defined herein, substituted with a cycloalkyl group, as defined herein. Non-limiting alkyl (cycloalkyl) groups include cyclopropylmethyl, cyclobutylmethyl, cyclopentylmethyl, cyclohexylmethyl and the like.

The term "halo" or "halogen" refers to fluoro, chloro, bromo and iodo.

The terms "haloalkyl" and "haloalkoxy" include structures of alkyl or alkoxy, and among them at least one hydrogen is replaced by a halogen atom. In certain embodiments, if two or more hydrogen atoms are replaced by halogen atoms, the halogen atoms are either the same or different from each other.

The term "cyano" as used herein refers to a radical of the formula —CN.

The term "carbonyl" is an organic functional group (C=O) formed by the bonding of two atoms of carbon and oxygen through a double bond.

The term "alkanoyl" or "alkylcarbonyl" refers to a carbonyl group further substituted with an alkyl group. Typical alkanoyl groups include, but are not limited to, acetyl, propionyl, butyryl, pentanoyl, hexanoyl, and the like.

The term "amino" refers to the group —NH$_2$. The term "alkylamino" refers to an amino substituent further substituted with one or two alkyl groups, in particular a group —NRR', wherein R and R' are each independently selected from hydrogen or lower alkyl, provided that —NRR' is not —NH$_2$. The term "aminoalkyl" refers to an alkyl substituent further substituted with one or more amino groups. The term "cyanoalkyl" refers to an alkyl substituent further substituted with one or more cyano groups. The term "heteroalkyl" as used herein means that one or more atoms of the backbone chains of the alkyl groups defined herein are heteroatoms, such as oxygen, nitrogen, sulfur, silicon, phosphorus or combinations thereof. The heteroatom(s) may be located anywhere within the heteroalkyl group or at a position where the heteroalkyl group is attached to the remainder of the molecule.

The term "heteroaryl" refers to an aryl group comprising one or more ring heteroatoms selected from the group consisting of nitrogen, oxygen and sulfur. The N-containing "heteroaryl" moiety means that at least one of the backbone atoms in the ring of the aryl group is nitrogen. Depending on the structure, a heteroaryl group may be a monovalent group or a divalent group (i.e., a heteroarylene group). Examples of heteroaryl groups include, but are not limited to, pyridyl, imidazolyl, pyrimidinyl, pyrazolyl, triazolyl, pyrazinyl, tetrazolyl, furyl, thienyl, isoxazolyl, thiazolyl, oxazole, isothiazolyl, pyrrolyl, quinolyl, isoquinolyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furyl, benzofuryl, benzothienyl, benzothiazolyl, benzoxazolyl, quinazolinyl, naphthyridyl and furopyridinyl and the like.

The term "heterocycloalkyl" as used herein means that one or more of the atoms constituting the ring in the non-aryl ring is a hetero atom selected from the group consisting of nitrogen, oxygen and sulfur. The heterocycloalkyl ring may be composed of three, four, five, six, seven, eight, nine or more than nine atoms. The heterocycloalkyl group can be optionally substituted. Examples of heterocycloalkyl groups include, but are not limited to, lactam, lactone, cyclic imine, cyclic thioimine, cyclic carbamate, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxetane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxol, 1,3-dioxolane, 1,3-dithiolelen, 1,3-dithiolane, isoxazoline, isoxazolidine, oxazoline, oxazolidine, oxazolidinone, thiazoline, thiazolidine and 1,3- oxathiolane. Depending on the structure, a heterocycloalkyl group may be a monovalent group or a divalent group (i.e., a heterocycloalkylene group).

The term "alkyl(heteroaryl)" refers to an alkyl group, as defined herein, substituted with an heteroaryl group, as defined herein.

The term "alkyl(heterocycloalkyl)" refers to an alkyl group, as defined herein, substituted with a heterocycloalkyl group, as defined herein.

The term "optionally substituted" or "substituted" means that the group mentioned may be substituted with one or more additional groups, each of which is individually and independently selected from alkyl, cycloalkyl, aryl, heteroaryl, heterocyclic group, hydroxy, alkoxy, cyano, halogen, amide, nitro, haloalkyl, amino, methylsulfonyl and the like.

As used herein, $GI_{50}$ refers to the concentration of a drug required to inhibit 50% of cell growth, that is, the concentration of a drug when the growth of 50% of cells (such as cancer cells) is inhibited or controlled.

As used herein, $IC_{50}$ refers to the amount, concentration or dose of a particular test compound at which 50% inhibition of the maximum effect is obtained in an assay that measures an effect.

CDK9 Kinase Inhibitor of the Invention

The invention relates to inhibitors of cyclin dependent kinases CDK9. In particular, in the present invention there is provided a compound of formula (I), or a pharmaceutically acceptable salt, solvate, ester, acid, metabolite or prodrug thereof:

(I)

wherein Y is selected from the group consisting of p-fluorobenzoyl, trans-4-aminocyclohexyl in which N is optionally substituted with $R_3$, and trans-4-aminocyclohexylmethyl in which N is optionally substituted with $R_3$;

Z is selected from the group consisting of NH, S and O;
$R_1$ is selected from the group consisting of hydrogen and halogen;
$R_2$ is selected from the group consisting of hydrogen, C1-C3 alkyl, C3-C6 cycloalkyl, C3-C6 heterocycloalkyl optionally substituted with $R_4$, and phenyl optionally substituted with $R_4$;
$R_3$ is selected from the group consisting of C2-C6 alkanoyl and C1-C3 alkoxy (C1-C3) alkyl;
$R_4$ is selected from the group consisting of cyano and halogen.

In certain preferred embodiments, Y is selected from the following structures:

In a preferred embodiment, $R_1$ is chlorine.

In another preferred embodiment, $R_2$ is selected from the group consisting of hydrogen, methyl, cyclopropyl, cyclohexyl, 4-tetrahydropyranyl optionally substituted with cyano, and phenyl optionally substituted with fluorine.

In another preferred embodiment, $R_3$ is selected from the group consisting of acetyl, 2-methoxyethyl, (R)-1-methyl-2-methoxyethyl, and (S)-1-methyl-2-methoxyethyl.

In the present invention, particularly preferred compounds include:

4-(((4-(5-chloro-2-(((1R,4r)-4-(((R)-1-methoxypropyl-2-yl)amino)cyclohexyl)amino) pyridin-4-yl) thiazol-2-yl)amino)methyl)tetrahydro-2H-pyran-4-carbonitrile (1r,4r)-$N^1$-(5-chloro-4-(2-(((tetrahydro-2H-pyran-4-yl)methyl)amino)thiazol-4-yl)pyridin-2-yl)cyclohexane-1,4-diamine N-((1r,4r)-4-((5-chloro-4-(2-(((tetrahydro-2H-pyran-4-yl)methyl)amino)thiazol-4-yl) pyridin-2-yl)amino) cyclohexyl)acetamide (1r,4r)-$N^1$-(5-chloro-4-(2-(((tetrahydro-2H-pyran-4-yl)methyl)amino)thiazol-4-yl)pyridin-2-yl)-$N^4$-(2-methoxyethyl)cyclohexyl-1,4-diamine (1S,4r)-$N^1$-(5-chloro-4-(2-(((tetrahydro-2H-pyran-4-yl)methyl)amino)thiazol-4-yl)pyridin-2-yl)-$N^4$-((S)-1-methoxypropan-2-yl)cyclohexyl-1,4-diamine (1R,4r)-$N^1$-(5-chloro-4-(2-(((tetrahydro-2H-pyran-4-yl)methyl)amino)thiazol-4-yl)pyridin-2-yl)-$N^4$-((R)-1-methoxypropan-2-yl)cyclohexane-1,4-diamine 4-(2-((((1r,4r)-4-aminocyclohexyl)methyl)amino)-5-chloropyridin-4-yl)-N-((tetrahydro-2H-pyran-4-yl) methyl)thiazol-2-amine N-(5-chloro-4-(2-(((tetrahydro-2H-pyran-4-yl) methyl)amino)thiazol-4-yl)pyridin-2-yl)-4-fluorobenzamide (1r,4r)-$N^1$-(5-chloro-4-(2-(methylamino)thiazol-4-yl) pyridin-2-yl)-$N^4$-(2-methoxyethyl)cyclohexane-1,4-diamine (1r,4r)-$N^1$-(5-chloro-4-(2-((cyclohexylmethyl) amino)thiazol-4-yl)pyridin-2-yl)-$N^4$-(2-methoxyethyl)cyclohexane-1,4-diamine (1r,4r)-$N^1$-(4-(2-(benzylamino)thiazol-4-yl)-5-chloropyridin-2-yl)-$N^4$-(2-methoxyethyl)cyclohexane-1,4-diamine (1r,4r)-N¹-(5-chloro-4-(2-((4-fluorobenzyl)amino)
thiazol-4-yl)pyridin-2-yl)-N⁴-(2-methoxyethyl)cy-
clohexane-1,4-diamine (1r,4r)-N¹-(5-chloro-4-(2-((cyclopropylmethyl)
amino)thiazol-4-yl)pyridin-2-yl)-N⁴-(2-methoxy-
ethyl)cyclohexane-1,4-diamine 4-((4-(5-chloro-2-(((1r,4r)-4-((2-methoxyethyl)
amino)cyclohexyl)amino)pyridin-4-yl)thiazol-2-
ylamino)methyl)tetrahydro-2H-pyran-4-carbonitrile 4-(((4-(5-chloro-2-(((1S,4r)-4-(((S)-1-methoxypro-
pyl-2-yl)amino)cyclohexyl)amino) pyridin-4-yl)
thiazol-2-yl)amino)methyl)tetrahydro-2H-pyran-4-
carbonitrile (1r,4r)-N¹-(5-chloro-4-(2-((tetrahydro-2H-pyran-4-
yl)methoxy)thiazol-4-yl)pyridin-2-yl)-N⁴-(2-
methoxyethyl)cyclohexane-1,4-diamine (1r,4r)-N¹-(5-chloro-4-(2-(((tetrahydro-2H-pyran-4-
yl)methyl)mercapto)thiazol-4-yl) pyridin-2-yl)-N⁴-
(2-methoxyethyl)cyclohexane-1,4-diamine (1r,4r)-N¹-(2-methoxyethyl)-N⁴-(4-(2-(((tetrahydro-
2H-pyran-4-yl)methyl)amino)thiazol-4-yl)pyridin-2-
yl)cyclohexane-1,4-diamine The structures of preferred compounds of the invention are listed below.

compound 1 compound 2 compound 3 compound 4

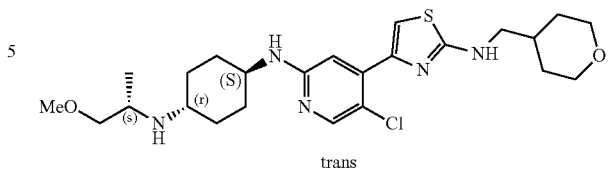

compound 5 trans

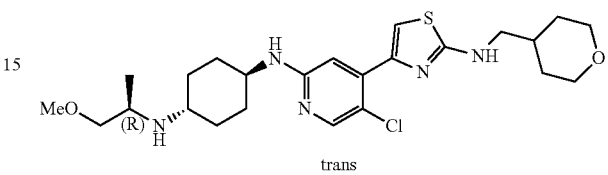

compound 6 trans

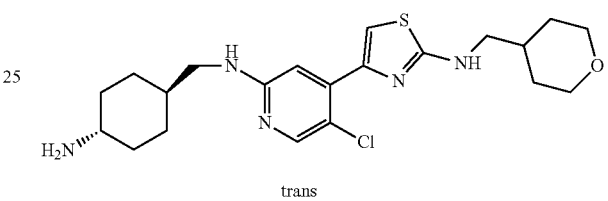

compound 7 trans

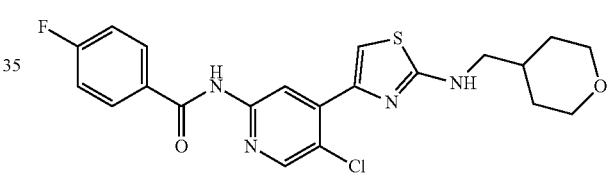

compound 8

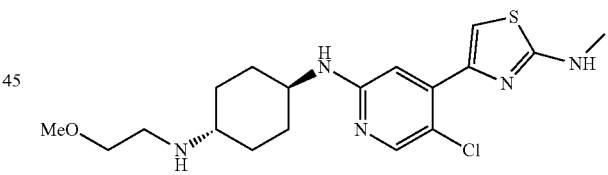

compound 9 trans

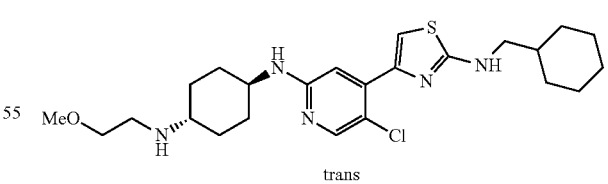

compound 10 trans

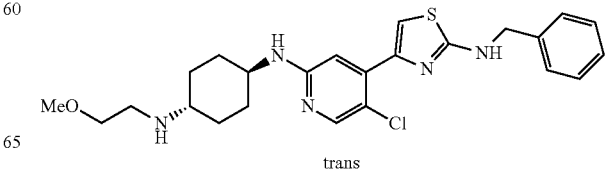

compound 11 trans

-continued

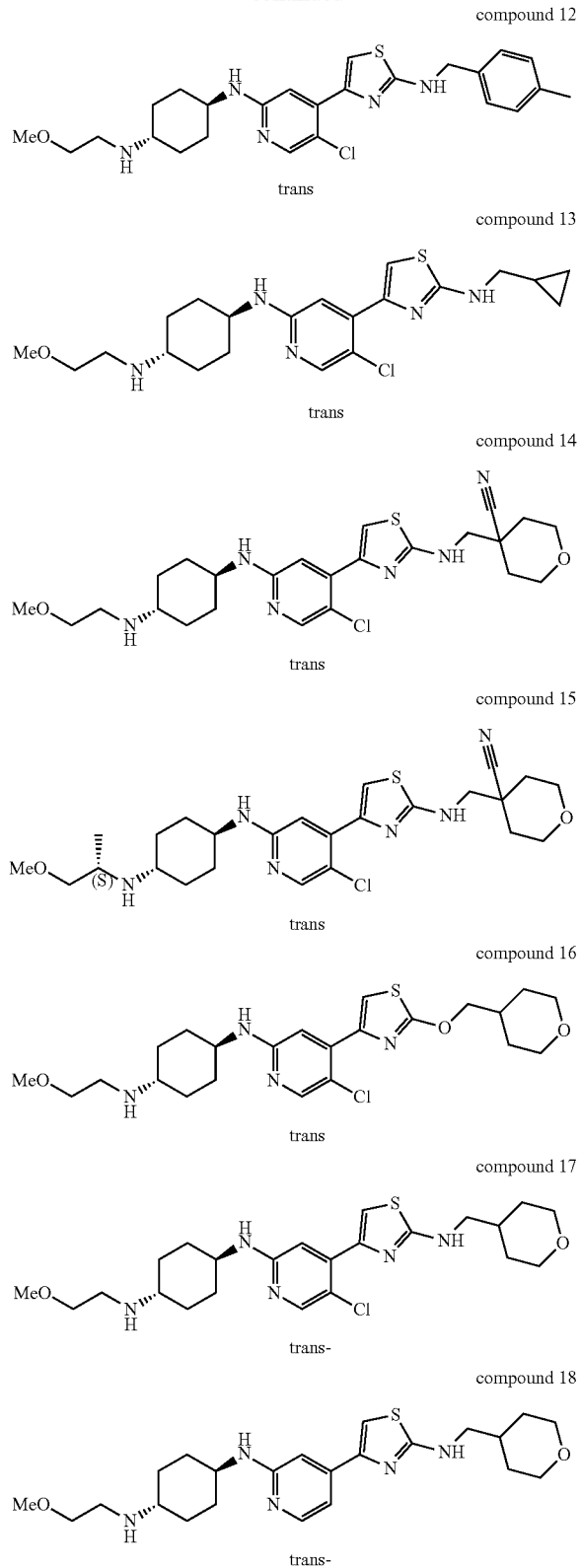

Although the above table lists the structures of preferred compounds of the present invention, it should be understood that the two carbon atoms respectively attached to the para-amino group on the cyclohexyl group are not chiral centers, the chemical bond representation of ╱ or ⋯ is merely indicative of attachment of the two chemical bonds to the para-amino group are trans-structured with respect to the cyclohexyl group, and thus the compounds represented by exchanging of these two chemical bonds ╱ and ⋯ are also within the scope of the present invention.

Described herein are novel kinase inhibitors. Pharmaceutically acceptable salts, solvates, esters, acids, pharmaceutically active metabolites and prodrugs of this compound are also described herein.

In additional or further embodiments, the compounds described herein are administered to a subject in need thereof to be metabolized in its body to produce metabolites which are then used to produce the desired effect, including the desired therapeutic effect.

The compounds described herein can be made into and/or used as pharmaceutically acceptable salts. Types of pharmaceutically acceptable salts include, but are not limited to: (1) an acid addition salt formed by reacting a free base form of the compound with a pharmaceutically acceptable inorganic acid, such as hydrochloric acid, hydrobromic acid, sulfuric acid, nitric acid, phosphoric acid, metaphosphoric acid, or the like; or with an organic acid, such as acetic acid, propionic acid, caproic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tert-butylacetic acid, glucoheptonic acid, 4,4'-methylene bis-(3-hydroxy-2-ene-1-carboxylic acid), 3-phenylpropionic acid, trimethylacetic acid, dodecyl sulfate, gluconic acid, glutamic acid, salicylic acid, hydroxynaphthoic acid, stearic acid, muconic acid, etc.; (2) a base addition salt formed when an acidic proton of a parent compound is replaced by a metal ion, such as an alkali metal ion (e.g., lithium, sodium, potassium), an alkaline earth metal ion (e.g., magnesium or calcium), or an aluminum ion; or coordinated with organic bases. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

Corresponding counterions of pharmaceutically acceptable salts can be analyzed and characterized using a variety of methods including, but not limited to, ion exchange chromatography, ion chromatography, capillary electrophoresis, inductively coupled plasma, atomic absorption spectroscopy, mass spectrometry, or any combination of them.

The salt is recovered using at least one of the following techniques: filtration, precipitation with a non-solvent followed by filtration, evaporation of the solvent, or lyophilization in the case of an aqueous solution.

Screening and characterization of pharmaceutically acceptable salts, polymorphs, and/or solvates can be accomplished using a variety of techniques including, but not limited to, thermal analysis, X-ray diffraction, spectroscopy, microscopy, and elemental analysis. Various spectral techniques used include, but are not limited to, Raman, FTIR, UVIS, and NMR (liquid and solid state). Various microscopy techniques include, but are not limited to, IR microscopy and Raman microscopy.

Pharmaceutical Composition of the Invention

In the present invention there is also provided a pharmaceutical composition comprising at least one compound of formula (I), or a pharmaceutically acceptable salt, solvate, ester, acid, pharmaceutically active metabolite or prodrug thereof, and a pharmaceutically acceptable carrier or excipient, and optionally other therapeutic agents.

During treatment, it may be used alone or in combination with one or more other therapeutic agents, as appropriate. The drug comprising a compound of the invention may be administered to a patient by at least one of injection, oral, inhalation, rectal and transdermal administration.

In an embodiment of the invention, when treating a patient in accordance with the present invention, the amount of a given drug depends on a number of factors, such as the particular dosage regimen, the type of disease or disorder and its severity, and the subject in need of treatment or the uniqueness of the host (e.g., body weight), however, depending on the particular circumstances, including, for example, the particular drug that has been employed, the route of administration, the condition being treated, and the subject or host being treated, the dosage administered can be decided by methods routinely known in the art. Generally, for use in the treatment for an adult, the dosage administered will typically range from 0.02 to 5000 mg/day, for example from about 1 to 1500 mg/day. The desired dose may conveniently be presented as a single dose, or concurrently (or in a short period of time) or in divided doses at appropriate intervals, such as two, three, four or more divided doses per day. It will be understood by those skilled in the art that although the above dosage ranges are given, the specific effective amount can be appropriately adjusted depending on the condition of the patient and in connection with the diagnosis of the physician.

Use of Drug of the Present Invention

A compound of formula (I), or a pharmaceutically acceptable salt, solvate, ester, acid, metabolite or prodrug thereof, or a pharmaceutical composition comprising them, can be used to inhibit the activity of cyclin-dependent kinases (CDK) and cyclins, especially the activity of CDK9. The compound of formula (I) or a pharmaceutically acceptable salt, solvate, ester, acid, metabolite or prodrug thereof can be used for the treatment or prevention of one or more diseases selected from the group consisting of non-small cell lung cancer, small cell lung cancer, lung adenocarcinoma, squamous cell lung carcinoma, pancreatic cancer, prostate cancer, bladder cancer, liver cancer, skin cancer, glioma, breast cancer, melanoma, malignant glioma, rhabdomyosarcoma, ovarian cancer, astrocytoma, Ewing's sarcoma, retinoblastoma, epithelial cell carcinoma, colon cancer, renal cancer, gastrointestinal stromal tumor, leukemia, histiocytic lymphoma, and nasopharyngeal carcinoma.

More preferably, the compound of formula (I) described herein, or a pharmaceutically acceptable salt, solvate, ester, acid, metabolite or prodrug thereof, or a pharmaceutical composition comprising them can be used as an inhibitor of CDK9, which can be used for treatment of non-small cell lung cancer, small cell lung cancer, lung adenocarcinoma, squamous cell lung carcinoma, pancreatic cancer, prostate cancer, bladder cancer, liver cancer, skin cancer, glioma, breast cancer, melanoma, malignant glioma, rhabdomyosarcoma, ovarian cancer, astrocytoma, Ewing's sarcoma, retinoblastoma, epithelial cell carcinoma, colon cancer, renal cancer, gastrointestinal stromal tumor, leukemia, histiocytic lymphoma, and nasopharyngeal carcinoma by using it alone or in combination with other therapeutic agents.

Preparation of Compound

Compounds of formula (I) can be synthesized using standard synthetic techniques known to those skilled in the art or using methods known in the art in combination with the methods described herein. Additionally, the solvents, temperatures, and other reaction conditions presented herein can vary depending on the skill of the art. As a further guide, the following synthetic methods can also be utilized.

The reactions can be used sequentially to provide the compounds described herein; or they can be used to synthesize fragments which are subsequently added by the methods described herein and/or methods known in the art.

In certain embodiments, there is provided herein are methods of preparing a serine kinase inhibitor compound described herein and methods of use thereof. In certain embodiments, the compounds described herein can be synthesized using the following synthetic schemes. Compounds can be synthesized by methods analogous to those described below, using the appropriate starting materials.

Starting materials for the synthesis of the compounds described herein can be synthesized or can be obtained from commercial sources. The compounds described herein and other related compounds having different substituents can be synthesized using techniques and starting materials known to those skilled in the art. The general methods of preparing the compounds disclosed herein can be derived from reactions known in the art, and the reactions can be modified to introduce various moieties in the molecules provided herein by reagents and conditions deemed appropriate by those skilled in the art.

If desired, the reaction product can be isolated and purified using conventional techniques including, but not limited to, filtration, distillation, crystallization, chromatography, and the like. These products can be characterized using conventional methods, including physical constants and spectral data.

Non-limiting examples of synthetic schemes for the preparation of compounds of formula (I) are described below.

EXAMPLES

The following specific non-limiting examples are only to be construed as illustrative and not limiting the disclosure in any way. Although no further details are described, it is believed that one skilled in the art can fully utilize the present disclosure based on the description herein.

Example 1: Synthesis of 4-(((4-(5-chloro-2-(((1R, 4r)-4-(((R)-1-methoxy propyl-2-yl)amino)cyclohexyl)amino)pyridin-4-yl)thiazol-2-yl)amino)methyl)tetrahydro-2H-pyran-4-carbonitrile

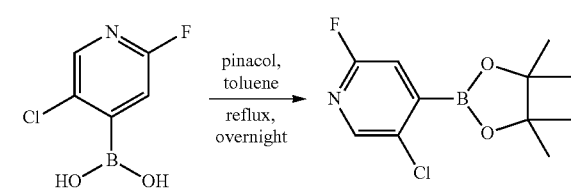

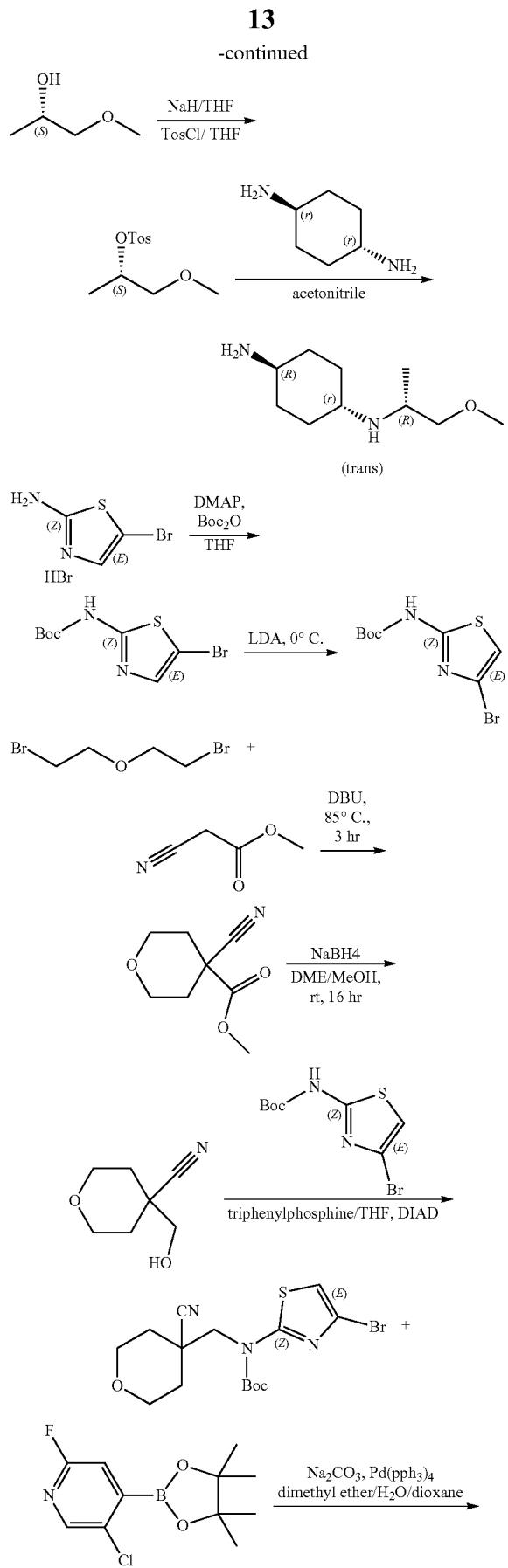

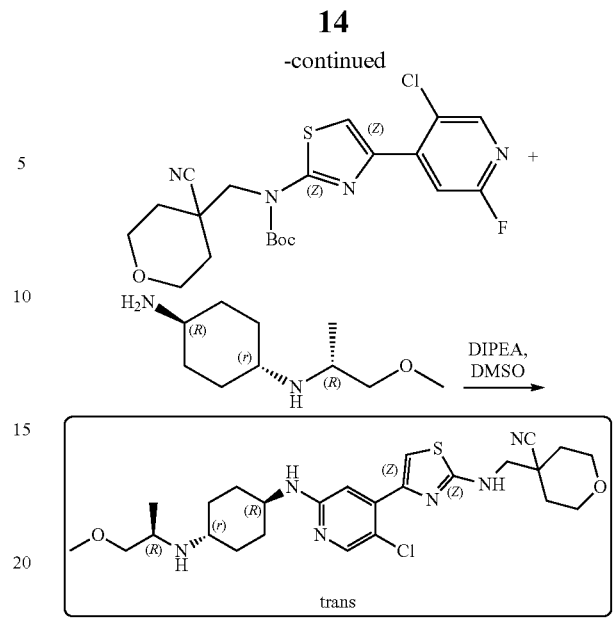

Step 1: Synthesis of 5-chloro-2-fluoro-4-(4,4,5,5-tetramethyl-1,3,2-dioxaborolan-2-yl)pyridine 5-chloro-2-fluoropyridine-4-boronic acid (0.7 g, 4.46 mmol) and pinacol (0.63 g, 5.35 mmol) were added to 50 mL of toluene, the mixture was warmed to 120° C. and refluxed overnight, and TLC showed a small amount of material remained. The reaction solution was cooled to room temperature, concentrated, and dried by oil pump to give 0.92 g of compound of 5-chloro-2-fluoro-4-(4,4,5,5-tetramethyl-1,3,2-dioxaborolan-2-yl)pyridine as a white solid, yield 80%, MS(ESI): m/z 258.1; (M+H)+.

Step 2: Synthesis of (S)-1-methoxypropan-2-yl 4-methylbenzenesulfonate

60% sodium hydride NaH (6.52 g, 283 mmol) was added to dry tetrahydrofuran THF (200 mL), which was cooled to 0° C. by an ice bath, and protected under nitrogen, and then (S)-(+)-1-methoxy-2-propanol (21 g, 233 mmol) was added dropwise. After the completion of the dropwise addition, the mixture was stirred at room temperature for 1.5 hours. The reaction solution was cooled again to 0° C., and a solution of p-toluenesulfonyl chloride (45.3 g, 283 mmol) in tetrahydrofuran THF (200 mL) was then added dropwise. After the addition, the mixture was stirred at room temperature overnight. TLC showed the starting material was completely consumed. The reaction mixture was diluted with ethyl acetate (500 mL), quenched by dropwise addition of water (500 mL) under ice-cooling, and separated. The aqueous phase was extracted once with ethyl acetate (200 mL). The organic phases were combined, washed with water (200 mL) and saturated brine (200 mL), dried over anhydrous sodium sulfate, filtered, and concentrated to give 43 g of a pale yellow oily crude product, which was isolated by column (petroleum ether/ethyl acetate=5/1) to give 37 g of (S)-1-methoxypropan-2-yl 4-methylbenzenesulfonate as pale yellow oil, yield 65.1%, MS(ESI): m/z 245.1; (M+H)+.

Step 3: Synthesis of (1r, 4R)-N¹-((R)-1-methoxypropan-2-yl) cyclohexane-1,4-diamine (S)-1-methoxypropan-2-yl 4-methylbenzenesulfonate (5 g, 20.5 mmol) and trans-1,4-cyclohexanediamine (5.84 g, 51.2 mmol) were added to 50 mL of acetonitrile, which was heated to 90° C. and reacted overnight. The reaction was followed with TLC till its completion. The reaction solution was cooled and then filtered, and the filtration was concentrated. The residue was dissolved in dichloromethane, mixed with silica gel and isolated by column (dichloromethane/methanol=10/1) to give 2.5 g of compound of (1r, 4R)-N$^1$-((R)-1-methoxypropan-2-yl)cyclohexane-1,4-diamine as a pale yellow liquid, yield 65%, MS(ESI): m/z 187.3; (M+H)$^+$.

Step 4: Synthesis of tert-butyl 5-bromothiazol-2-ylcarbamate 5-bromothiazol-2-amine hydrobromide (105 g, 403 mmol) was suspended in 500 mL of tetrahydrofuran, and dimethylaminopyridine (2.41 g, 20 mmol) was added to form a white turbidity. A solution of di-tert-butyl dicarbonate (105.6 g, 484.6 mmol) in tetrahydrofuran was slowly added dropwise. The mixture was reacted for two days. Then the reaction solution was concentrated, dissolved in dichloromethane (300 mL), mixed with silica gel and isolated by column (eluted with petroleum ether/ethyl acetate=10/1–6/1 gradient) to give 45 g of tert-butyl 5-bromothiazol-2-ylcarbamate as an off-white solid, yield 40%, MS(ESI): m/z 278.98; (M+H)$^+$.

Step 5: Synthesis of tert-butyl 4-bromothiazol-2-ylcarbamate

A solution of diisopropylamine (64 ml, 446 mmol) in 200 mL of tetrahydrofuran was added to a dry three-neck bottle, which was protected under nitrogen, and cooled to 0° C., and then n-butyllithium (2.5M, 173 ml, 431.7 mmol) was added. The reaction was conducted for 1 hour after addition was completed. A solution of tert-butyl 5-bromothiazol-2-ylcarbamate in 400 mL of tetrahydrofuran was added dropwise at 0° C., and the reaction was conducted for 2 hours after addition was completed. TLC showed the reaction was completed. At 0° C., the reaction was quenched by slow addition of ice water (5 mL), stirred for 30 min, then saturated ammonium chloride (500 mL) aqueous solution was added, and separated. The aqueous layer was extracted with dichloromethane (2×300 mL). The organic phases were combined, washed with saturated brine, dried over anhydrous sodium sulfate, filtered, and concentrated. The residue was recrystallized with petroleum ether: ethyl acetate=30:1 to give 31 g of tert-butyl 4-bromothiazol-2-ylcarbamate as a white solid, yield 77.5%, MS(ESI): m/z 278.98; (M+H)$^+$.

Step 6: Synthesis of 4-cyano-tetrahydro-2H-pyran-4-methyl carbonate

Methyl cyanoacetate (39.1 g, 395.3 mmol) and 2, 2-dibromoethyl ether (100 g, 434.8 mmol) were added to 600 mL of dimethylformamide, and DBU (90 g, 593 mmol) was added. The mixture was heated at 85° C. for 3 hours. TLC showed the starting material was completely consumed. The mixture was filtered to remove the solid, which was washed with ethyl acetate (2×300 mL). The filtrate was concentrated to give a brown oil, which was dstillated under reduced pressure. The fraction was received when the internal temperature is 65-70° C., which was a colorless liquid, and placed to crystallization to give 42 g of 4-cyano-tetrahydro-2H-pyran-4-methyl carbonate as a white solid, yield 62.8%, MS(ESI): m/z 178.2; (M+H)$^+$.

Step 7: Synthesis of 4-(hydroxymethyl)-tetrahydro-2H-pyran-4-carbonitrile 4-cyano-tetrahydro-2H-pyran-4-methyl carbonate (42 g, 248.4 mmol) was dissolved in 400 ml of ethylene glycol dimethyl ether and 40 ml of methanol, which was cooled to 0° C. in an ice bath, and sodium borohydride (11.1 g, 149 mmol) was added in portions. After the completion of addition, the mixture was naturally warmed to room temperature and stirred for 16 hours. TLC showed the reaction was completed. Then the reaction solution was concentrated, then concentrated again after the addition of methanol to quench the excess sodium borohydride, and then concentrated. The residue was isolated by column (petroleum ether/ethyl acetate=5/1) to give 28 g of 4-(hydroxymethyl)-tetrahydro-2H-pyran-4-carbonitrile as a pale yellow oil, yield 79.5%, MS(ESI): m/z 142.1; (M+H)$^+$.

Step 8: synthesis of tert-butyl (4-bromothiazol-2-yl) ((4-cyanotetrahydro-2H-pyran-4-yl)methyl)carbamate 4-(hydroxymethyl)-tetrahydro-2H-pyran-4-carbonitrile, tert-butyl 4-bromo thiazol-2-ylcarbamate and triphenylphosphine were added to anhydrous tetrahydrofuran THF, which was cooled to 0° C., and then diisopropyl azodicarboxylate DIAD was added dropwise. The mixture was stirred at room temperature for 10 minutes, and then warmed to 40° C. and stirred overnight. Then the reaction solution was concentrated. The residue was dissolved in dichloromethane, mixed with silica gel and isolated by column (petroleum ether/ethyl acetate=50/1, 30/1, 20/1) to give 365 mg of tert-butyl (4-bromothiazol-2-yl)((4-cyanotetrahydro-2H-pyran-4-yl)methyl)carbamate as a white solid, yield 50%, MS(ESI): m/z 402.1; (M+H)$^+$.

Step 9: synthesis of tert-butyl (4-(5-chloro-2-fluoropyridin-4-yl)thiazol-2-yl) ((4-cyano-tetrahydro-2H-pyran-4-yl)methyl)carbamate 5-chloro-2-fluoro-4-(4,4,5,5-tetramethyl-1,3,2-dioxaborolan-2-yl)pyridine and sodium carbonate were added in a mixture of dimethyl ether/H$_2$O/dioxane, which was replaed with nitrogen twice, and then tert-butyl (4-bromothiazol-2-yl) ((4-cyanotetrahydro-2H-pyran-4-yl)methyl)carbamate and tetratriphenylphosphine palladium Pd(pph$_3$)$_4$ were added. The system was replaed with nitrogen three times, then warmed up to 70° C., and reacted for 6 hours. When TLC showed only half of the starting material remained, the heating was stopped, and the reaction was treated. The reaction solution was cooled to room temperature, and then ethyl acetate and methanol were added. The mixture was filtered, the cake was washed with ethyl acetate, and the filtrate was concentrated. The residue was then dissolved in dichloromethane, washed with saturated brine, and separated. The organic phase was dried over anhydrous sodium sulfate, and filtered. The filtrate was mixed with silica gel and isolated by column (petroleum ether/ethyl acetate=30/1) to give 3.2 g of tert-butyl (4-(5-chloro-2-fluoropyridin-4-yl)thiazol-2-yl)((4-cyano-tetrahydro-2H-pyran-4-yl)methyl)carbamate as white foamy solid, yield 55%, MS(ESI): m/z 453.1; (M+H)$^+$.

Step 10: synthesis of 4-(((4-(5-chloro-2-(((1R,4r)-4-(((R)-1-methoxypropyl-2-yl)amino)cyclohexyl) amino)pyridin-4-yl)thiazol-2-yl)amino)methyl)tetrahydro- 2H-pyran-4-carbonitrile Tert-butyl (4-(5-chloro-2-fluoropyridin-4-yl)thiazol-2-yl) ((4-cyano-tetrahydro-2H-pyran-4-yl)methyl)carbamate (3.2 g, 7.1 mmol), (1r, 4R)-N$^1$-((R)-1-methoxypropan-2-yl)cyclohexane-1,4-diamine (3.9 g, 21.2 mmol) and diisopropylethylamine DIPEA were added to 30 mL of dimethyl sulfoxide, which was protected under nitrogen, and then warmed up to 100-110° C. and reacted for two days. The reaction was monitored by TLC and LCMS. When the starting material of tert-butyl (4-(5-chloro-2-fluoropyridin-4-yl)thiazol-2-yl)((4-cyano-tetrahydro-2H-pyran-4-yl)methyl)carbamate was completely consumed and some of the intermediates with the removal of BOC remained, the reaction was stopped. The reaction mixture was cooled and then diluted with ethyl acetate (60 mL), water (150 mL) was added under ice-cooling, and separated. The aqueous phase was then extracted with ethyl acetate (2×50 mL). The organic phases were combined, washed with saturated brine (100 mL), dried over anhydrous sodium sulfate, filtered, and the filtrate was concentrated to give a crude as a yellowish brown oil. The crude was isolated by column (acetonitrile/water/trifluoroacetic acid=80/20/0.001) to give 700 mg of 4-(((4-(5-chloro-2-(((1R,4r)-4-(((R)-1-methoxypropyl-2-yl)amino)cyclohexyl)amino)pyridin-4-yl)thiazol-2-yl)amino)methyl)tetrahydro-2H-pyran-4-carbonitrile as a pale yellow solid, yield 19.1%. $^1$H NMR (400 MHz, CDCl$_3$) δ 8.06; (s, 1H), 7.38; (s, 1H), 6.97; (s, 1H), 5.92; (brs, 1H), 4.45; (d, J=8.0 Hz, 1H), 4.02; (dd, J1=2.8 Hz, J2=12 Hz, 2H), 3.71-3.74; (m, 4H), 3.54-3.56; (m, 1H), 3.35; (s, 3H), 3.21-3.25; (m, 2H), 3.00-3.05; (m, 1H), 2.50-2.60; (m, 1H), 2.15; (d, J=9.6 Hz, 2H), 2.04-2.07; (m, 1H), 1.95; (d, J=12.8 Hz, 3H), 1.74-1.82; (m, 3H), 1.10-1.30; (m, 4H), 1.00; (d, J=8.4 Hz, 3H), MS(ESI): m/z 519.3; (M+H)$^+$.

Example 2: synthesis of (1r,4r)-M-(5-chloro-4-(2-(((tetrahydro-2H-pyran-4-yl)methyl)amino)thiazol-4-yl)pyridin-2-yl)cyclohexane-1,4-diamine

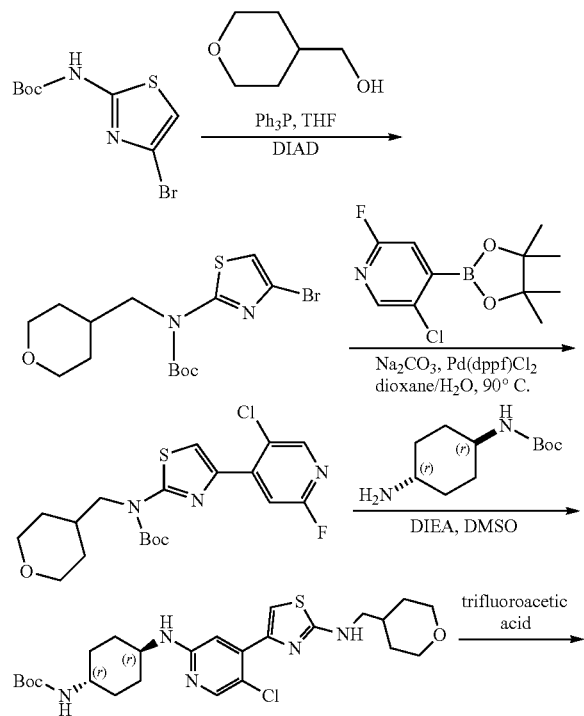

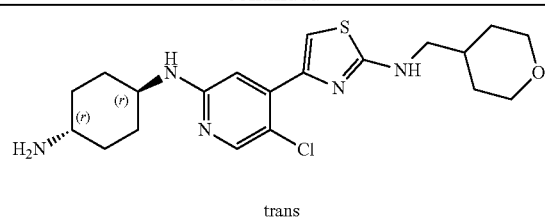

trans

Step 1: synthesis of tert-butyl (4-bromothiazol-2-yl)((tetrahydro-2H-pyran-4-yl)methyl)carbamate Tert-butyl 4-bromothiazole-2-carbamate (12.53 g, 107.91 mmol), (tetrahydro-2H-pyran-4-yl)methanol (20 g, 71.94 mmol) and triphenylphosphine were added to 360 mL of anhydrous THF (re-distilled), which was cooled to −10° C., and then diisopropyl azodicarboxylate DIAD (21.82 g, 107.91 mmol) was added. The mixture was stirred at room temperature for 10 minutes, and then warmed up to 50° C. and reacted for 3 hours. TLC showed the disappearance of the starting materials. Then the reaction solution was concentrated. The residue was dissolved in dichloromethane, mixed with silica gel and isolated by column (petroleum ether/ethyl acetate=30/1, 20/1) to give 21 g of tert-butyl (4-bromothiazol-2-yl)((tetrahydro-2H-pyran-4-yl)methyl) carbamate as a white solid, yield 87.5%, MS(ESI): m/z 519.3; (M+H)$^+$.

Step 2: synthesis of tert-butyl (4-(5-chloro-2-fluoropyridin-4-yl)thiazol-2-yl) ((tetrahydro-2H-pyran-4-yl)methyl)carbamate Tert-butyl (4-bromothiazol-2-yl)((tetrahydro-2H-pyran-4-yl)methyl) carbamate (21 g, 1.51 mmol), 5-chloro-2-fluoro-4-(4,4,5,5-tetramethyl-1,3,2-dioxaborolan-2-yl)pyridine (30 g, 3.0 mmol), Pd(dppf)Cl$_2$ (2.04 g, 0.151) and Na$_2$CO$_3$ (15 g, 3.78 mmol) were added to 500 mL of dioxane and 100 mL of water, which was protected under nitrogen, then warmed up to 90° C. and reacted overnight. The reaction was monitored by TLC and LCMS. When tert-butyl (4-bromothiazol-2-yl)((tetrahydro-2H-pyran-4-yl)methyl) carbamate was completely consumed, the reaction was stopped. The reaction solution was cooled and then water (100 mL) was added. The mixture was extracted with ethyl acetate (3×100 mL). The organic phases were combined, dried over anhydrous sodium sulfate, filtered, and concentrated to give a crude as a yellowish brown oil. The residue was isolated by chromatography (petroleum ether/ethyl acetate=30:1, 25:1) to give 19.4 g of tert-butyl (4-(5-chloro-2-fluoropyridin-4-yl)thiazol-2-yl)((tetrahydro-2H-pyran-4-yl)methyl)carbam ate as a white solid, yield 81.5%, MS(ESI): m/z 428.1; (M+H)$^+$.

Step 3: synthesis of tert-butyl ((1r,4r)-4-((5-chloro-4-(2-(((tetrahydro-2H-pyran-4-yl)methyl)amino)thiazol-4-yl)pyridin-2-yl)amino)cyclohexyl) carbamate Tert-butyl (4-(5-chloro-2-fluoropyridin-4-yl)thiazol-2-yl)((tetrahydro-2H-pyran-4-yl)methyl)carbamate and tert-butyl (1r, 4r)-(4-aminocyclohexyl) carbamate was added to DMSO, and diisopropylethylamine DIEA was added. The mixture was warmed up to 100° C. and reacted for 2 days. When TLC showed the starting materials disappeared, the heating was stopped, and the reaction was treated. The reaction solution was cooled to room temperature, and poured into ice water. The mixture was extracted with dichloromethane (3×200 mL). The organic phase was washed with saturated brine, dried over anhydrous sodium sulfate, and filtered. The filtrate was mixed with silica gel and isolated by column (petroleum ether/ethyl acetate=3/1, 2:1, 1:1) to give 3.6 g of tert-butyl ((1r,4r)-4-((5-chloro-4-(2-(((tetrahydro-2H-pyran-4-yl)methyl)amino)thiazol-4-yl)pyridin-2-yl)amino)cyclohexyl)carbamate as a pale yellow solid, yield 40%, MS(ESI): m/z 522.2; (M+H)$^+$.

Step 4: synthesis of (1r,4r)-N$^1$-(5-chloro-4-(2-(((tetrahydro-2H-pyran-4-yl) methyl)amino)thiazol-4-yl)pyridin-2-yl)cyclohexane-1,4-diamine Tert-butyl ((1r,4r)-4-((5-chloro-4-(2-(((tetrahydro-2H-pyran-4-yl)methyl) amino)thiazol-4-yl)pyridin-2-yl)amino) cyclohexyl)carbamate (2.9 g, 5.56 mmol) was added to tetrahydrofuran/dichloromethane (20 mL/20 mL), which was protected under nitrogen and cooled to 0° C., then 20 mL of trifluoroacetic acid was added dropwise. The mixture was reacted for 2 h at room temperature. The reaction was monitored by TLC. The reaction solution was concentrated, and then poured into ice water slowly. The mixture was extracted with dichloromethane (3×30 mL). The organic phase was washed with saturated brine, dried over sodium sulfate, filtered, and concentrated to give a crude. The crude was beated with dichloromethane: ethyl acetate=2:1, filtered, and dried to give 1.6 g of (1r,4r)-N$^1$-(5-chloro-4-(2-(((tetrahydro-2H-pyran-4-yl)methyl)amino)thiazol-4-yl)pyridin-2-yl)cyclohexane-1,4-diamine as a white solid, yield 68%, $^1$H NMR (400 MHz, CDCl$_3$) δ 8.06; (s, 1H), 7.33; (s, 1H), 6.96; (s, 1H), 5.21-5.30; (m, 1H), 4.32; (d, J=8.0 Hz, 1H)), 3.99-4.03; (m, 2H), 3.53-3.61; (m, 1H), 3.38-3.44; (m, 2H), 3.23; (t, J=6.4 Hz, 2H), 2.68-2.74; (m, 1H), 2.11-2.13; (m, 2H), 1.85-2.13; (m, 3H), 1.70-1.73; (m, 2H), 1.10-1.45; (m, 7H). MS(ESI): m/z 422.2; (M+H)$^+$.

Example 3: synthesis of N-((1r,4r)-4-((5-chloro-4-(2-(((tetrahydro-2H-pyran-4-yl)methyl)amino)thiazol-4-yl)pyridin-2-yl)amino)cyclohexyl)acetamide

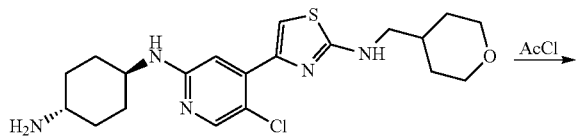

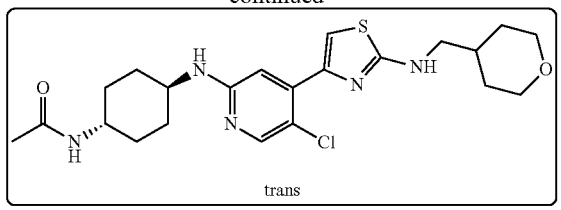

(1r,4r)-N$^1$-(5-chloro-4-(2-(((tetrahydro-2H-pyran-4-yl)methyl)amino)thiazol-4-yl)pyridin-2-yl)cyclohexane-1,4-diamine (0.422 g, 1 mmol) was dissolved in 10 mL of dichloromethane, which was protected under nitrogen, and acetyl chloride was added. A large amount of solids precipitated and TLC showed that the starting material was completely consumed. The mixture was filtered, beated with methyl tert-butyl ether, and dried to give 187 mg of N-((1r,4r)-4-((5-chloro-4-(2-(((tetrahydro-2H-pyran-4-yl)methyl)amino)thiazol-4-yl)pyridin-2-yl)amino)cyclohexyl)acetamide as a white solid, yield 41%, $^1$H NMR (400 MHz, CDCl$_3$) δ 8.06 (s, 1H), 7.33; (s, 1H), 6.96; (s, 1H), 5.30-5.34; (m, 1H), 5.20-5.30; (m, 1H), 4.32; (d, J=8.0 Hz, 1H), 3.99-4.03; (m, 2H), 3.78-3.83; (m, 1H), 3.62-3.64; (m, 1H), 3.41; (t, J=12 Hz, 2H), 3.24; (t, J=6.4 Hz, 1H), 2.13-2.15; (m, 2H), 2.00-2.09; (m, 2H), 1.95; (s, 3H), 1.70-1.73; (m, 2H), 1.20-1.49; (m, 7H). MS(ESI): m/z 464.1; (M+H)$^+$.

Example 4: synthesis of (1r,4r)-N$^1$-(5-chloro-4-(2-(((tetrahydro-2H-pyran-4-yl)methyl)amino)thiazol-4-yl)pyridin-2-yl)-N$^4$-(2-methoxyethyl)cyclohexane-1,4-diamine

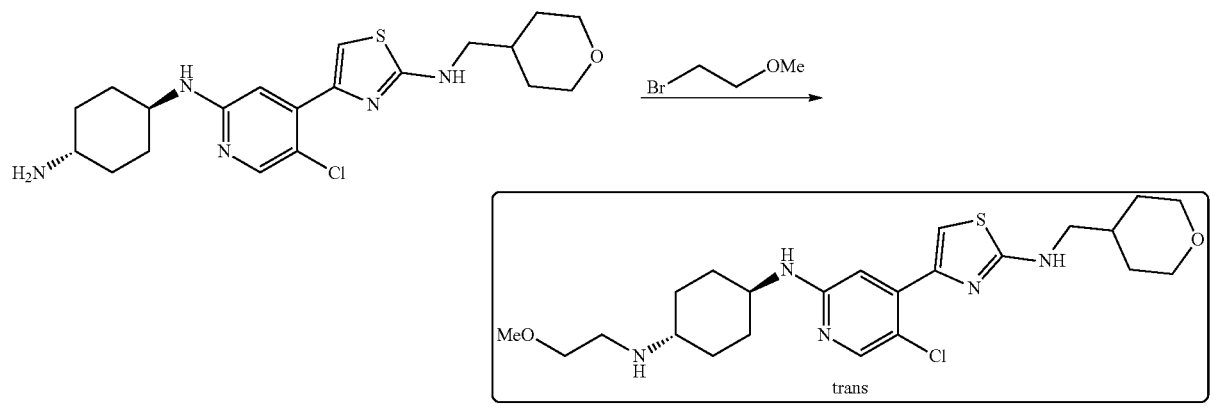

(1r,4r-N$^1$-(5-chloro-4-(2-(((tetrahydro-2H-pyran-4-yl)methyl)amino)thiazol-4-yl)pyridin-2-yl)cyclohexane-1,4-diamine (0.357 g, 0.846 mmol), 2-bromoethyl methyl ether (0.118 g, 0.846 mmol) and potassium carbonate (0.116 g, 0.846 mmol) were added to 10 mL DMF, which was protected under nitrogen, and then warmed up to 100° C. and reacted for two days. The reaction was monitored by TLC and LCMS, and treated after the reaction was stopped. The reaction solution was cooled and then poured into ice water (20 mL). The mixture was extracted with ethyl acetate (3×20 mL). The organic phase was washed with saturated brine, dried over anhydrous sodium sulfate, filtered, and concentrated to give a crude as a yellowish brown oil. The residue was isolated by column chromatography (dichloromethane/methanol=20:1, 15:1, 10:1) to give 0.070 g of (1r,4r-N$^1$-(5-chloro-4-(2-(((tetrahydro-2H-pyran-4-yl)methyl)amino)thiazol-4-yl) pyridin-2-yl)-N$^4$-(2-methoxyethyl)cyclohexane-1,4-diamine as a pale yellow solid, yield 17%, $^1$H NMR (400 MHz, CDCl$_3$) δ 8.06; (s, 1H), 7.33; (s, 1H), 6.96; (s, 1H), 5.65; (brs, 1H), 4.40; (d, J=8.0 Hz, 1H), 3.95-4.06; (m, 2H), 3.49-3.70; (m, 3H), 3.28-3.45; (m, 5H), 3.18; (t, J=6.4 Hz, 1H), 2.96-3.05; (m, 2H), 2.76-2081; (m, 1H), 2.14-2.28; (m, 6H), 1.85-1.95; (m, 3H), 1.70-1.73; (m, 2H), 1.41-1.60; (m, 2H), 1.13-1.40; (m, 5H). MS(ESI): m/z 480.3; (M+H)$^+$.

Example 5: synthesis of (1S,4r)-N$^1$-(5-chloro-4-(2-(((tetrahydro-2H-pyran-4-yl)methyl)amino)thiazol-4-yl)pyridin-2-yl)-N$^4$-((S)-1-methoxypropan-2-yl)cyclohexane-1,4-diamine acetate (30 mL). The organic phases were combined, washed with saturated brine (50 mL), dried over anhydrous sodium sulfate, filtered, and concentrated to give a crude as a pale yellow oil. The crude was isolated by column (petroleum ether/ethyl acetate=5/1) to give 4.2 g of (R)-1-methoxypropan-2-ol 4-methylbenzenesulfonate as pale yellow oil, yield 52%, MS(ESI): m/z 245.1; (M+H)$^+$.

Step 2: synthesis of (1S, 4r)-N$^1$-(5-chloro-4-(2-(((tetrahydro-2H-pyran-4-yl) methyl)amino)thiazol-4-yl)pyridin-2-yl)-N$^4$-((S)-1-methoxypropan-2-yl)cyclohexane-1,4-diamine (1r,4r)-N$^1$-(5-chloro-4-(2-(((tetrahydro-2H-pyran-4-yl)methyl)amino)thiazol-4-yl)pyridin-2-yl)cyclohexane-1,4-diamine (600 mg, 1.2 mmol), (R)-1-methoxy propan-2-ol

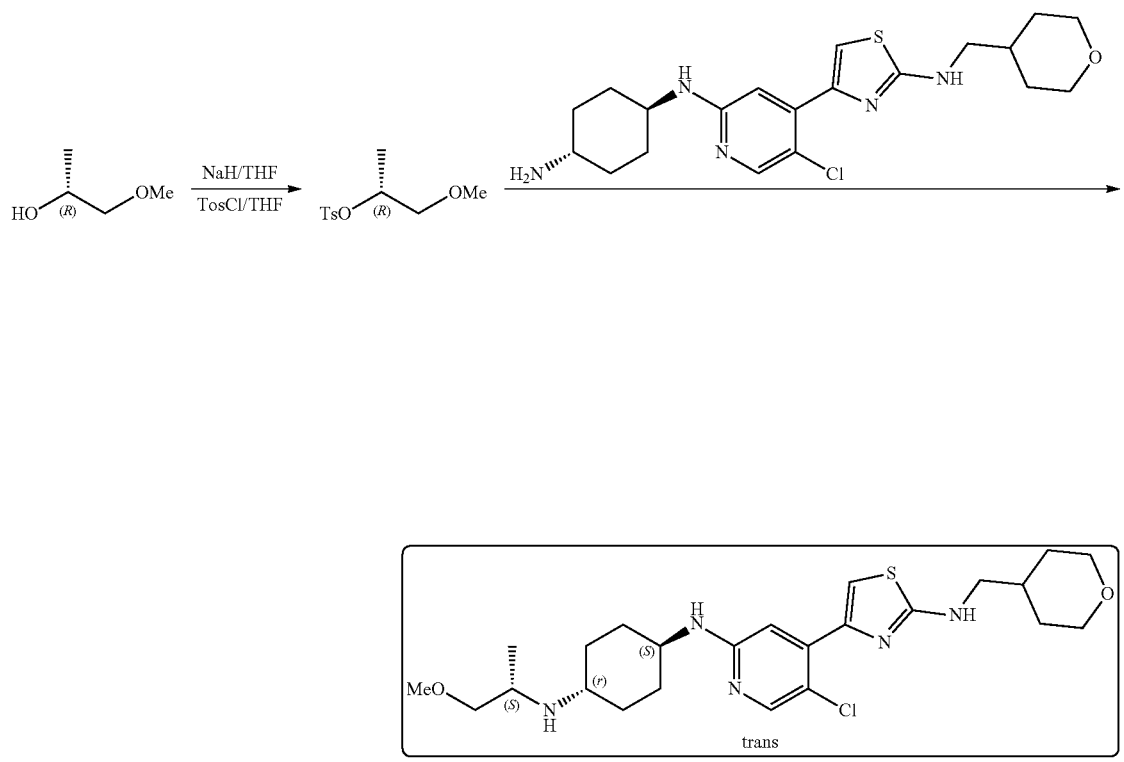

Step 1: synthesis of (R)-1-methoxypropan-2-ol 4-methylbenzenesulfonate

Sodium hydride NaH (1.46 g, 0.037 mmol) was added to dry tetrahydrofuran THF (1 L), which was cooled to 0° C. under ice-cooling and protected under nitrogen, and then (R)-(-)-1-methoxypropan-2-ol (3 g, 0.033 mmol) was added dropwise. After the completion of the dropwise addition, the mixture was warmed up to room temperature and stirred for 1.5 hours. The reaction solution was cooled again to 0° C., and a solution of p-toluenesulfonyl chloride TosCl (6.47 g, 0.034 mmol) in tetrahydrofuran THF (80 mL) was then added dropwise. The temperature was below 10° C. during the addition. After the addition, the mixture was stirred at room temperature (32° C.) overnight. TLC showed the starting material was completely consumed. The reaction was quenched by dropwise addition of saturated aqueous ammonium chloride (20 mL) under ice-cooling and separated. The aqueous phase was extracted twice with ethyl 4-methylbenzenesulfonate (293 mg, 1.42 mmol) and potassium carbonate (327 mg, 2.4 mmol) were added to 20 mL of acetonitrile, which was protected under nitrogen and warmed up to 90° C. and stirred overnight. The reaction was monitored by LC-MS. The reaction solution was cooled to room temperature, filtered, and concentrated to give a crude as a pale yellow oil. The crude was isolated by thick preparation plate (dichloromethane/methanol=8/1) to give 30 mg of (1S,4r)-N$^1$-(5-chloro-4-(2-(((tetrahydro-2H-pyran-4-yl)methyl)amino)thiazol-4-yl)pyridin-2-yl)-N$^4$-((S)-1-methoxypropan-2-yl)cyclohexane-1,4-diamine as a white solid, yield 4.3%, $^1$H NMR (600 MHz, CDCl$_3$) δ 8.06; (s, 1H), 7.29; (s, 1H), 6.96; (s, 1H), 5.59; (brs, 1H), 4.36; (d, J=8.0 Hz, 1H), 3.95-4.06; (m, 2H), 3.49-3.65; (m, 2H), 3.40-3.49; (m, 1H), 3.22-3.39; (m, 6H), 3.11-3.20; (m, 2H), 2.95-3.10; (m, 1H), 2.08-2.30; (m, 4H), 1.79-1.96; (m, 2H), 1.62-1.71; (m, 2H), 1.09-1.40; (m, 12H), 0.72-0.98; (m, 2H). MS(ESI): m/z 494.3; (M+H)$^+$.

Example 6: synthesis of (1R,4r)-N$^1$-(5-chloro-4-(2-(((tetrahydro-2H-pyran-4-yl)methyl)amino)thiazol-4-yl)pyridin-2-yl)-N$^4$-((R)-1-methoxypropan-2-yl)cyclohexane-1,4-diamine

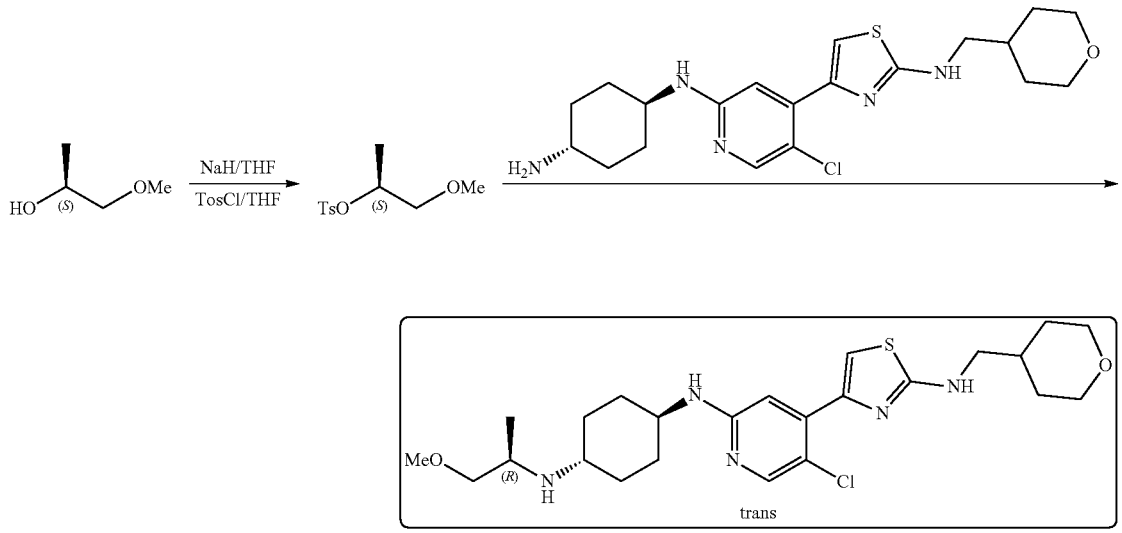

Step 1: synthesis of (S)-1-methoxypropan-2-ol 4-methylbenzenesulfonate

Sodium hydride NaH (60%, 1.46 g, 0.037 mol) was added to dry tetrahydrofuran THF (1 L), which was cooled to 0° C. under ice-cooling and protected under nitrogen, and then (S)-(+)-1-methoxypropan-2-ol (3 g, 0.033 mol) was added dropwise. After the completion of the dropwise addition, the mixture was warmed up to room temperature and stirred for 1.5 hours. The reaction solution was cooled again to 0° C., and a solution of p-toluenesulfonyl chloride TosCl in tetrahydrofuran THF was then added dropwise. The temperature was below 10° C. during the addition. After the addition, the mixture was stirred at room temperature (32° C.) overnight. TLC showed the starting material was completely consumed. The reaction was quenched by dropwise addition of saturated aqueous ammonium chloride (20 mL) under ice-cooling and separated. The aqueous phase was extracted twice with ethyl acetate (30 mL). The organic phases were combined, washed with saturated brine (50 mL), dried over anhydrous sodium sulfate, filtered, and concentrated to give a crude as a pale yellow oil. The crude was isolated by column (petroleum ether/ethyl acetate=5/1) to give 4.5 g of (S)-1-methoxypropan-2-ol 4-methylbenzenesulfonate as pale yellow oil, yield 55%, MS(ESI): m/z 245.1; (M+H)$^+$.

Step 2: synthesis of (1R, 4r)-M-(5-chloro-4-(2-(((tetrahydro-2H-pyran-4-yl)methyl) amino)thiazol-4-yl)pyridin-2-yl)-N$^4$-((R)-1-methoxypropan-2-yl)cyclohexane-1,4-diamine (1r,4r)-M-(5-chloro-4-(2-((((tetrahydro-2H-pyran-4-yl)methyl)amino)thiazol-4-yl)pyridin-2-yl)cyclohexane-1,4-diamine (422 mg, 1 mmol), (S)-1-methoxypropan-2-ol 4-methylbenzenesulfonate (122 mg, 0.5 mmol) and potassium carbonate (276 mg, 2 mmol) were added to 15 mL of acetonitrile, which was protected under nitrogen, and warmed up to 90° C. and stirred overnight. The reaction was monitored by LC-MS till it was completed 25%. The reaction solution was cooled to room temperature, filtered, and concentrated to give a crude as a pale yellow oil. The crude was isolated by thick preparation plate (dichloromethane/methanol=8/1) to give 83 mg of (1R,4r)-N$^1$-(5-chloro-4-(2-(((tetrahydro-2H-pyran-4-yl)methyl)amino)thiazol-4-yl)pyridin-2-yl)-N$^4$-((R)-1-methoxypropan-2-yl)cyclohexane-1,4-diamine as a white solid, yield 17%, $^1$H NMR (400 MHz, CDCl$_3$) δ 8.06; (s, 1H), 7.33; (s, 1H), 6.96; (s, 1H), 5.30; (brs, 1H), 4.37; (d, J=8.0 Hz, 1H), 3.99-4.03; (m, 2H), 3.52-3.59; (m, 1H), 3.25-3.49; (m, 4H), 3.36; (s, 3H), 3.16-3.25; (m, 2H), 3.06-3.10; (m, 1H), 2.60-2.65; (m, 1H), 2.16; (d, J=10.8 Hz, 2H), 2.00-2.08; (m, 2H), 1.89-1.95; (m, 2H), 1.33-1.45; (m, 4H), 1.12-1.29; (m, 4H), 1.07; (d, J=6.4 Hz, 3H). MS(ESI): m/z 494.2; (M+H)$^+$.

Example 7: synthesis of 4-(2-((((1r,4r)-4-aminocyclohexyl)methyl) amino)-5-chloropyridin-4-yl)-N-((tetrahydro-2H-pyran-4-yl)methyl)thiazol-2-amine

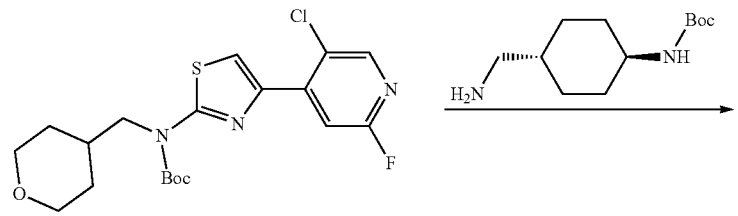

-continued

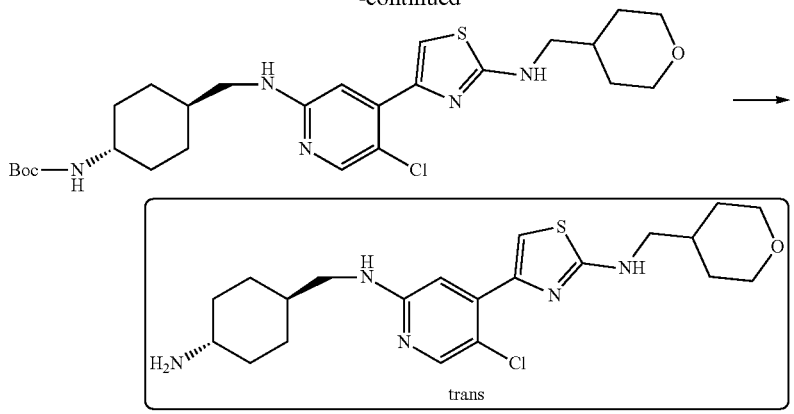

Step 1: synthesis of tert-butyl ((1r, 4r)-4-(((5-chloro-4-(2-(((tetrahydro-2H-pyran-4-yl)methyl)amino)thiazol-4-yl)pyridin-2-yl)amino)methyl)cyclohexyl)carbamate Tert-butyl (4-(5-chloro-2-fluoropyridin-4-yl)thiazol-2-yl)((tetrahydro-2H-pyran-4-yl)methyl)carbamate (0.7 g, 1.6 mmol), tert-butyl (1r, 4r)-4-(aminomethyl) cyclohexylcarbamate (0.748 g, 3.2 mmol) and triethylamine (0.458 g, 4.8 mmol) was added to 10 mL of dimethyl sulfoxide. The mixture was heated to 110° C. and stirred for 48 hours. TLC showed the starting material was completely consumed. After being gcooled to room temperature, the reaction solution was poured into ice water. The mixture was extracted with ethyl acetate (3×20 mL). The organic phases were combined, washed with saturated brine, dried over anhydrous sodium sulfate, filtered, and concentrated. The residue was isolated by column chromatography (petroleum ether/ethyl acetate=10:1, 2:1) to give tert-butyl ((1r,4r)-4-(((5-chloro-4-(2-(((tetrahydro-2H-pyran-4-yl)methyl)amino)thiazol-4-yl)pyridin-2-yl)amino)methyl)cyclohexyl) carbamate as a yellow solid, yield 26%, MS(ESI): m/z 536.2; (M+H)+.

Step 2: synthesis of 4-(2-(((((1r, 4r)-4-aminocyclohexyl)methyl)amino)-5-chloropyridin-4-yl)-N-((tetrahydro-2H-pyran-4-yl)methyl)thiazol-2-amine Tert-butyl ((1r, 4r)-4-(((5-chloro-4-(2-(((tetrahydro-2H-pyran-4-yl)methyl)amino) thiazol-4-yl)pyridin-2-yl)amino) methyl)cyclohexyl)carbamate (230 mg, 0.43 mmol) was added to dichloromethane (10 mL), which was protected under nitrogen, and cooled to 0° C., and then trifluoroacetic acid was added dropwise. The mixture was reacted for 1 h at room temperature. The reaction was monitored by TLC. The reaction solution was concentrated, and then poured into ice water slowly. The mixture was extracted with dichloromethane (3×30 mL). The organic phase was washed with saturated brine, dried over sodium sulfate, filtered, and concentrated to give a crude. The crude was isolated by thick preparation plate (dichloromethane/methanol=5/1) to give 0.065 g of 4-(2-(((((1r, 4r)-4-aminocyclohexyl)methyl)amino)-5-chloropyridin-4-yl)-N-((tetrahydro-2H-pyran-4-yl)methyl)thiazol-2-amine as a pale yellow oil, yield 34.8%, ¹H NMR (400 MHz, MeOD) δ 7.82; (s, 1H), 7.11; (s, 1H), 6.95; (s, 1H), 3.84-3.88; (m, 2H), 3.32; (t, J=11.2 Hz, 2H), 3.16-3.17; (m, 2H), 3.16; (d, J=6.8 Hz, 2H), 3.04; (d, J=6.8 Hz, 2H), 2.75-2.80; (m, 1H), 1.81-1.92; (m, 5H), 1.61-1.64; (m, 2H), 1.49-1.51; (m, 1H), 1.12-1.29; (m, 5H), 0.92-1.05; (m, 2H). MS(ESI): m/z 436.3; (M+H)+.

Example 8: Synthesis of N-(5-chloro-4-(2-(((tetrahydro-2H-pyran-4-yl) methyl)amino)thiazol-4-yl) pyridin-2-yl)-4-fluorobenzamide

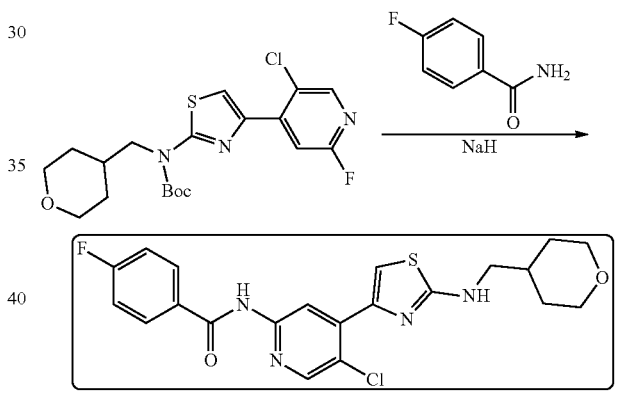

4-fluorobenzamide (0.65 g, 4.68 mmol) was dissolved in N, N-dimethylformamide DMF (15 mL), and NaH (0.19 g, 4.68 mmol) was added at room temperature. The reaction solution was stirred at room temperature for 10 min, and then tert-butyl (4-(5-chloro-2-fluoropyridin-4-yl)thiazol-2-yl((tetrahydro-2H-pyran-4-yl)methyl)carbam ate (1 g, 2.34 mmol) was added. The reaction solution was warmed up to 55° C. and reacted for 4 h. The reaction was monitored by TLC. The reaction was stopped, and then the reaction solution was poured into water, and extracted with EA (3×20 mL). The organic phase was washed with saturated brine, dried over sodium sulfate, filtered, and concentrated to give a crude. The crude was isolated by thick preparation plate (PE:EA=1:1) to give 0.032 g of N-(5-chloro-4-(2-(((tetrahydro-2H-pyran-4-yl)methyl)amino)thiazol-4-yl)pyridin-2-yl)-4-fluorobenzamide as a white solid, yield 3.1%, ¹H NMR (400 MHz, CDCl₃) δ 8.96; (s, 1H), 8.52; (s, 1H), 8.30; (s, 1H), 7.93-7.96; (m, 2H), 7.41; (s, 1H), 7.19; (t, J=8.4 Hz, 2H), 5.35-5.38; (m, 1H), 4.00-4.04; (m, 2H), 3.40-3.50; (m, 2H), 3.24; (t, J=6.4 Hz, 2H), 1.95-2.01; (m, 1H), 1.72-1.76; (m, 2H), 1.36-1.45; (m, 2H). (ESI+): m/z 447.1; [M+H]+.

Example 9: Synthesis of (1r, 4r)-N¹-(5-chloro-4-(2-(methylamino)thiazol-4-yl)pyridin-2-yl)-M-(2-methoxyethyl)cyclohexane-1,4-diamine

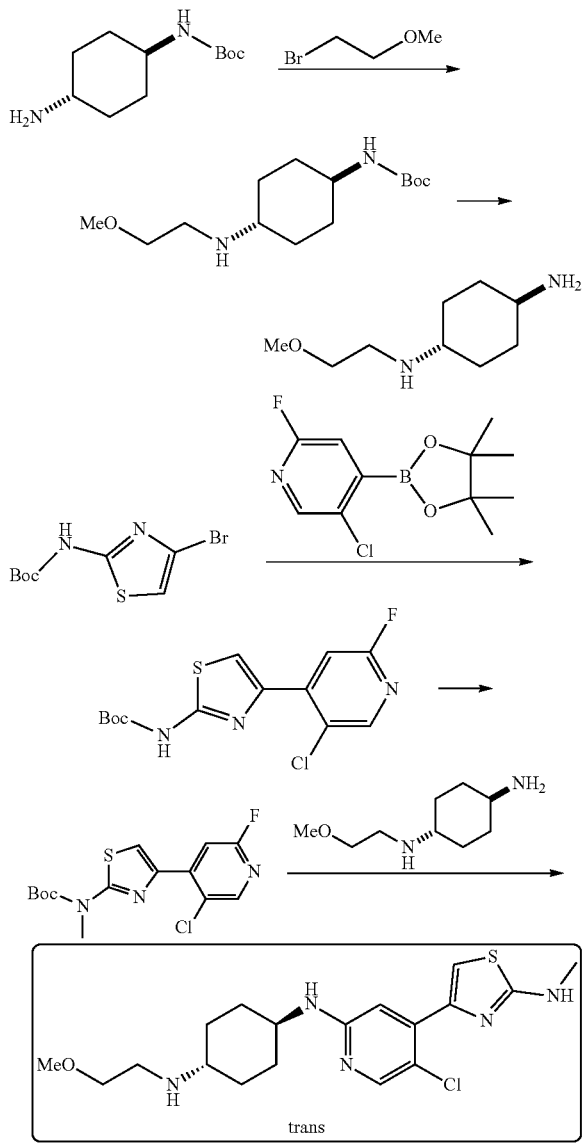

Step 1: synthesis of tert-butyl ((1r, 4r)-4-((2-methoxyethyl)amino)cyclohexyl) carbamate Tert-butyl (1r, 4r)-(4-aminocyclohexyl)carbamate (10.0 g, 46.7 mmol), 2-bromoethylmethylether (5.2 g, 37.4 mmol) and potassium carbonate (12.9 g, 93.4 mmol) were added to acetonitrile (150 mL). The reaction was stirred at 80° C. for 16 h. The reaction was monitored by TLC. When few of the starting material remained, the reaction was stopped. The reaction solution was cooled to room temperature and filtered. The filtrate was dried by rotary evaporation, mixed with silica gel and isolated by silica gel column chromatography (dichloromethane/methanol=20:1) to give 6.3 g of tert-butyl ((1r, 4r)-4-((2-methoxyethyl)amino)cyclohexyl) carbamate as a yellowish white solid. yield 50%, MS(ESI): m/z 273.2; (M+H)⁺.

Step 2: synthesis of (1r, 4r)-N¹-(2-methoxyethyl)cyclohexane-1,4-diamine

Tert-butyl ((1r, 4r)-N¹-((2-methoxyethyl)amino)cyclohexyl)carbamate (6 g, 22.0 mmol) was dissolved in dilute hydrochloric acid-tetrahydrofuran (80 mL). The reaction was stirred at room temperature for 2 h and a large amount of solid precipitated. The reaction solution was filtered. The cake was dried to obtained 5.1 g of (1r, 4r)-N¹-(2-methoxyethyl)cyclohexane-1,4-diamine (dihydrochloride) as a white solid, yield 94.8%, MS(ESI): m/z 173.2; (M+H)⁺.

Step 3: synthesis of Tert-butyl (4-(5-chloro-2-fluoropyridin-4-yl)thiazol-2-yl) carbamate Tert-butyl 4-bromothiazol-2-yl carbamate (20.0 g, 71.7 mmol), 5-chloro-2-fluoro-4-(4,4,5,5-tetramethyl-1,3,2-dioxaborolan-2-yl)pyridine (37.0 g, 143.4 mmol), Pd(dppf)Cl₂ (2.6 g, 0.151) and Na₂CO₃ (22.8 g, 245 mmol) were dissolved in 1,4-dioxane/H₂O (350 mL/40 mL), which was replaced with nitrogen for three times and then stirred at 90° C. for 16 h. The reaction was monitored by LCMS. The starting materials remained a few and 5-chloro-2-fluoro-4-(4,4,5,5-tetramethyl-1,3,2-dioxaborolan-2-yl)pyridine (18.5 g, 71.7 mmol) was further added. The reaction was replaced with nitrogen for three times and stirred at 85° C. for additional 18 h. The reaction was monitored by LCMS. About 95% of the starting materials have been converted into products. The reaction solution was cooled to room temperature and filtered. The filtrate was dried by rotary evaporation, mixed with silica gel and isolated by silica gel column chromatography (petroleum ether/ethyl acetate=10:1) to give 11.0 g of tert-butyl (4-(5-chloro-2-fluoropyridin-4-yl)thiazol-2-yl)carbamate as a white solid, yield 47%, and another 10 g of crude product. MS(ESI): m/z 330.0; (M+H)⁺.

Step 4: synthesis of Tert-butyl (4-(5-chloro-2-fluoropyridin-4-yl)thiazol-2-yl) (methyl)carbamate Tert-butyl (4-(5-chloro-2-fluoropyridin-4-yl)thiazol-2-yl) carbamate (200 mg, 0.61 mmol) and triphenylphosphine (239 mg, 0.91 mmol) were dissolved in THF (4 mL), which was replaced with nitrogen for three times, and methanol MeOH (78 mg, 2.43 mmol) was added. The mixture was stirred at room temperature for 1 minute, and then diisopropyl azodicarboxylate DIAD (184 mg, 0.91 mmol) was added. The reaction was stirred at room temperature for 2 h. TLC showed the starting material was completely consumed. The reaction solution was isolated by preparation TLC chromatograph with a developing solvent of petroleum ether/ethyl acetate=10:1 to give 205 mg of tert-butyl (4-(5-chloro-2-fluoropyridin-4-yl)thiazol-2-yl)(methyl)carbamate as a white solid, yield 98%, MS(ESI): m/z 344.1; (M+H)⁺.

Step 5: synthesis of (1r, 4r)-N¹-(5-chloro-4-(2-(methylamino)thiazol-4-yl)pyridin-2-yl)-N⁴-(2-methoxyethyl)cyclohexane-1,4-diamine Tert-butyl (4-(5-chloro-2-fluoropyridin-4-yl)thiazol-2-yl)(methyl)carbamate (200 mg, 0.58 mmol), (1r, 4r)-N¹-(2-methoxyethyl)cyclohexane-1,4-diamine (150 mg, 0.64 mmol), diisopropylethylamine DIEA (375 mg, 2.9 mol), and cesium fluoride (265 mg, 1.74 mmol) were dissolved in dimethyl sulfoxide (3 mL). The reaction was stirred at 120° C. for 2 days. The reaction was monitored by LCMS. When product generated, water (40 mL) was added to the reaction solution. The mixture was extracted with ethyl acetate (2×30 mL). The extract was dried over anhydrous sodium sulfate, concentrated by rotary evaporation, and then isolated by preparation TLC chromatography with a developing solvent of dichloromethane/methanol=6:1 to give 80 mg of (1r, 4r)-$N^1$-(5-chloro-4-(2-(methylamino)thiazol-4-yl)pyridin-2-yl)-$N^4$-(2-methoxy ethyl)cyclohexane-1,4-diamine as a pale yellow solid, yield 35%, $^1$H NMR (400 MHz, DMSO) δ 7.97; (s, 1H), 7.61-7.62; (m, 1H), 7.29; (s, 1H), 7.04; (s, 1H), 6.70; (d, J=7.6 Hz, 1H), 3.59-3.61; (m, 2H), 3.37-3.42; (m, 3H), 3.25; (s, 3H), 2.87; (d, J=4.8 Hz, 2H), 2.74-2.77; (m, 2H), 1.90-1.96; (m, 4H), 1.12-1.23; (m, 4H). (ESI+): m/z 396.2; [M+H]$^+$.

Example 10: Synthesis of (1r, 4r)-$N^1$-(5-chloro-4-(2-((cyclohexylmethyl) amino)thiazol-4-yl)pyridin-2-yl)-$N^4$-(2-methoxyethyl)cyclohexane-1,4-diamine

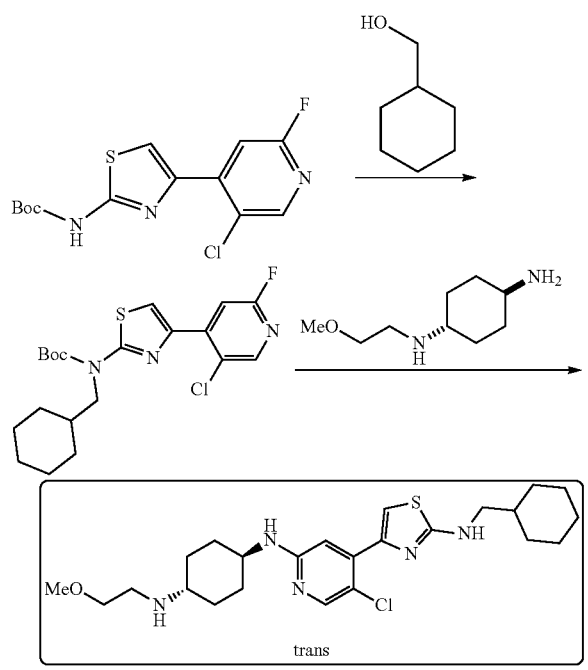

Step 1: synthesis of tert-butyl (4-(5-chloro-2-fluoropyridin-4-yl)thiazol-2-yl) (cyclohexylmethyl)carbamate Tert-butyl (4-(5-chloro-2-fluoropyridin-4-yl)thiazol-2-yl) carbamate (200 mg, 0.61 mmol) and triphenylphosphine (239 mg, 0.91 mmol) were dissolved in THF (5 mL), which was replaced with nitrogen for three times, and cyclohexylmethanol (207 mg, 1.82 mmol) was added. The mixture was stirred at room temperature for 5 minute, and then diisopropyl azodicarboxylate DIAD (184 mg, 0.91 mmol) was added. The reaction was stirred at room temperature for 2 h. TLC showed the starting material was completely consumed. The reaction solution was isolated by preparation TLC chromatograph with a developing solvent of petroleum ether/ethyl acetate=10:1 to give 255 mg of tert-butyl (4-(5-chloro-2-fluoropyridin-4-yl)thiazol-2-yl)(cyclohexylmethyl) carbamate as a white solid, yield 99%, (ESI+): m/z 426.1; [M+H]$^+$.

Step 2: synthesis of (1r, 4r)-$N^1$-(5-chloro-4-(2-((cyclohexylmethyl)amino) thiazol-4-yl)pyridin-2-yl)-$N^4$-(2-methoxyethyl)cyclohexane-1,4-diamine Tert-butyl (4-(5-chloro-2-fluoropyridin-4-yl)thiazol-2-yl) (cyclohexylmethyl) carbamate (250 mg, 0.59 mmol), (1r, 4r)-$N^1$-(2-methoxyethyl) cyclohexane-1,4-diamine (288 mg, 1.17 mmol), diisopropylethylamine DIEA (379 mg, 2.93 mol), and cesium fluoride (268 mg, 1.76 mmol) were dissolved in dimethyl sulfoxide (8 mL). The reaction was stirred at 120° C. for 2 days. The reaction was monitored by LCMS. When product generated, water (30 mL) was added to the reaction solution. The mixture was extracted with dichloromethane/isopropanol=3:1 (2×30 mL). The extract was washed with brine, dried over anhydrous sodium sulfate, concentrated by rotary evaporation, then mixed with silica gel and isolated by silica gel column chromatography (dichloromethane/methanol=50:1→20:1) to give a crude as yellow oil. The crude was isolated by preparation TLC chromatography with a developing solvent of dichloromethane/methanol=8:1 to give 100 mg of (1r, 4r)-$N^1$-(5-chloro-4-(2-(cyclohexylmethyl)amino)thiazol-4-yl)pyridin-2-yl)-$N^4$-(2-methoxyethyl)cyclohexane-1,4-diamine as a pale yellow solid, yield 30%, $^1$H NMR (400 MHz, DMSO) δ 7.97; (s, 1H), 7.67-7.69; (m, 1H), 7.25; (s, 1H), 7.01; (s, 1H), 6.71; (d, J=7.6 Hz, 1H), 3.50-3.53; (m, 1H), 3.36-3.47; (m, 2H), 3.13; (t, J=6.0 Hz, 2H), 2.94-2.97; (m, 2H), 2.72-2.81; (m, 1H), 1.99-2.02; (m, 4H), 1.61-1.77; (m, 5H), 1.19-1.33; (m, 7H), 0.91-1.01; (m, 2H). (ESI+): m/z 478.3; [M+H]$^+$.

Example 11: Synthesis of (1r, 4r)-$N^1$-(4-(2-(benzylamino)thiazol-4-yl)-5-chloropyridin-2-yl)-$N^4$-(2-methoxyethyl)cyclohexane-1,4-diamine

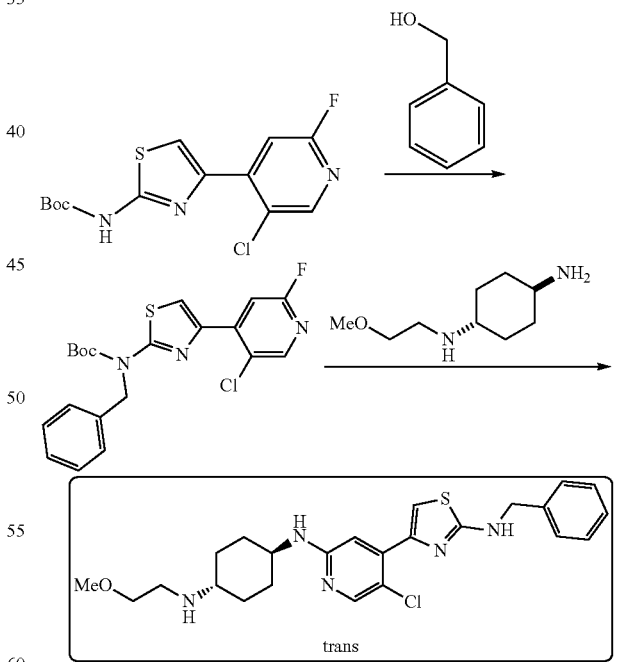

Step 1: synthesis of tert-butyl benzyl (4-(5-chloro-2-fluoropyridin-4-yl) thiazol-2-yl)carbamate Tert-butyl (4-(5-chloro-2-fluoropyridin-4-yl)thiazol-2-yl) carbamate (200 mg, 0.61 mmol) and triphenylphosphine (239 mg, 0.91 mmol) were dissolved in THF (5 mL), which was replaced with nitrogen for three times, and then benzyl alcohol (131 mg, 1.21 mmol) was added. The mixture was stirred at room temperature for 5 minute, and then diisopropylethylamine DIEA (184 mg, 0.91 mmol) was added. The reaction was stirred at room temperature for 2 h. TLC showed the starting material was completely consumed. The reaction solution was isolated by preparation TLC chromatograph with a developing solvent of petroleum ether/ethyl acetate=8:1 to give 246 mg of tert-butyl benzyl (4-(5-chloro-2-fluoropyridin-4-yl)thiazol-2-yl)carbamate as a white solid, yield 97%, (ESI+): m/z 420.1; [M+H]$^+$.

Step 2: synthesis of (1r, 4r)-N$^1$-(4-(2-(benzylamino) thiazol-4-yl)-5-chloropyridin-2-yl)-N$^4$-(2-methoxyethyl)cyclohexane-1,4-diamine Tert-butyl benzyl (4-(5-chloro-2-fluoropyridin-4-yl)thiazol-2-yl)carbamate (240 mg, 0.57 mmol), (1r, 4r)-N$^1$-(2-methoxyethyl)cyclohexane-1,4-diamine (280 mg, 1.14 mmol), diisopropylethylamine DIEA (369 mg, 2.86 mol), and cesium fluoride (268 mg, 1.71 mmol) were dissolved in dimethyl sulfoxide (8 mL). The reaction was stirred at 120° C. for 3 days. The reaction was monitored by LCMS. When product generated, water (30 mL) was added to the reaction solution. The mixture was extracted with dichloromethane/isopropanol=3:1 (2×35 mL). The extract was washed with brine, dried over anhydrous sodium sulfate, concentrated by rotary evaporation, then mixed with silica gel and isolated by silica gel column chromatography (dichloromethane/methanol=20:1) to give a crude as yellow oil. The crude was isolated by preparation TLC chromatography with a developing solvent of dichloromethane/methanol=6:1 to give 100 mg of (1r,4r)-N$^1$-(4-(2-(benzylamino) thiazol-4-yl)-5-chloropyridin-2-yl)-N$^4$-(2-methoxyethyl)cyclohexane-1,4-diamine as a pale yellow solid, yield 30%, $^1$H NMR (400 MHz, DMSO) δ 8.21; (t, J=6.0 Hz, 1H), 7.98; (s, 1H), 7.26-7.40; (m, 6H), 7.05; (s, 1H), 6.72; (d, J=7.6 Hz, 1H), 4.52; (d, J=5.6 Hz, 2H), 3.46-3.53; (m, 4H), 2.97; (brs, 2H), 2.81; (brs, 1H), 1.99-2.01; (m, 4H), 1.18-1.34; (m, 4H). (ESI+): m/z 472.1; [M+H]$^+$.

Example 12: Synthesis of (1r, 4r)-N$^1$-(5-chloro-4-(2-((4-fluorobenzyl)amino) thiazol-4-yl)pyridin-2-yl)-N$^4$-(2-methoxyethyl)cyclohexane-1,4-diamine

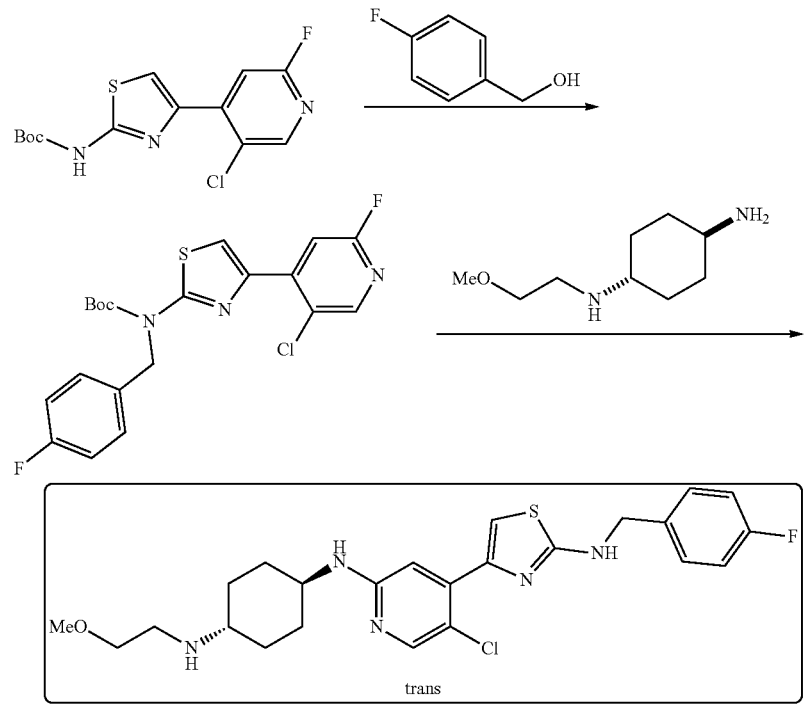

Step 1: synthesis of tert-butyl (4-(5-chloro-2-fluoropyridin-4-yl)thiazol-2-yl) (4-fluorobenzyl)carbamate Tert-butyl (4-(5-chloro-2-fluoropyridin-4-yl)thiazol-2-yl) carbamate (200 mg, 0.61 mmol) and triphenylphosphine (239 mg, 0.91 mmol) were dissolved in THF (5 mL), which was replaced with nitrogen for three times, and then 4-fluorobenzyl alcohol (153 mg, 1.21 mmol) was added. The mixture was stirred at room temperature for 5 minute, and then DIAD (184 mg, 0.91 mmol) was added. The reaction was stirred at room temperature for 2 h. TLC showed the starting material was completely consumed. The reaction solution was isolated by preparation TLC chromatograph with a developing solution of PE/EA=10:1 to give 248 mg of tert-butyl (4-(5-chloro-2-fluoropyridin-4-yl)thiazol-2-yl) (4-fluorobenzyl)carbamate as a pale yellow solid, yield 93%, (ESI+): m/z 438.1; [M+H]$^+$.

Step 2: synthesis of (1r, 4r)-N$^1$-(5-chloro-4-(2-((4-fluorobenzyl)amino) thiazol-4-yl)pyridin-2-yl)-N$^4$-(2-methoxyethyl)cyclohexane-1,4-diamine Tert-butyl (4-(5-chloro-2-fluoropyridin-4-yl)thiazol-2-yl) (4-fluorobenzyl) carbamate (240 mg, 0.55 mmol), (1r, 4r)-N$^1$-(2-methoxyethyl) cyclohexane-1,4-diamine (268 mg, 1.10 mmol), diisopropylethylamine DIEA (353 mg, 2.74 mol), and cesium fluoride (251 mg, 1.65 mmol) were dissolved in dimethyl sulfoxide/N,N-dimethylacetamide (3 mL/3 mL). The reaction was stirred at 120° C. for 3 days. The reaction was monitored by LCMS. When product generated, water (35 mL) was added to the reaction solution. The mixture was extracted with dichloromethane/isopropanol=3:1 (2×30 mL). The extract was washed with brine, dried over anhydrous sodium sulfate, concentrated by rotary evaporation, then mixed with silica gel and isolated by silica gel column chromatography (dichloromethane/methanol=20:1) to give a crude as yellow oil. The crude was isolated by preparation TLC chromatography with a developing solvent of dichloromethane/methanol=8:1 to give 100 mg of (1r, 4r)-N$^1$-(5-chloro-4-(2-((4-fluorobenzyl))amino) thiazol-4-yl)pyridin-2-yl)-N$^4$-(2-methoxyethyl)cyclohexane-1,4-diamine as a pale yellow solid, yield 30%, $^1$H NMR (400 MHz, DMSO) δ 8.22-8.24; (m, 1H), 7.98; (s, 1H), 7.41-7.44; (m, 2H), 7.32; (s, 1H), 7.18; (t, J=8.8 Hz, 2H), 7.04; (s, 1H), 6.73; (d, J=7.6 Hz, 1H), 4.50; (d, J=5.6 Hz, 2H), 3.52-3.55; (m, 3H), 3.29; (s, 3H), 2.96; (brs, 2H), 2.97; (brs, 1H), 1.98-2.01; (m, 4H), 1.21-1.23; (m, 4H). (ESI+): m/z 490.2; [M+H]$^+$.

Example 13: Synthesis of (1r, 4r)-N$^1$-(5-chloro-4-(2-((cyclopropylmethyl) amino)thiazol-4-yl)pyridin-2-yl)-N$^4$-(2-methoxyethyl)cyclohexane-1,4-diamine

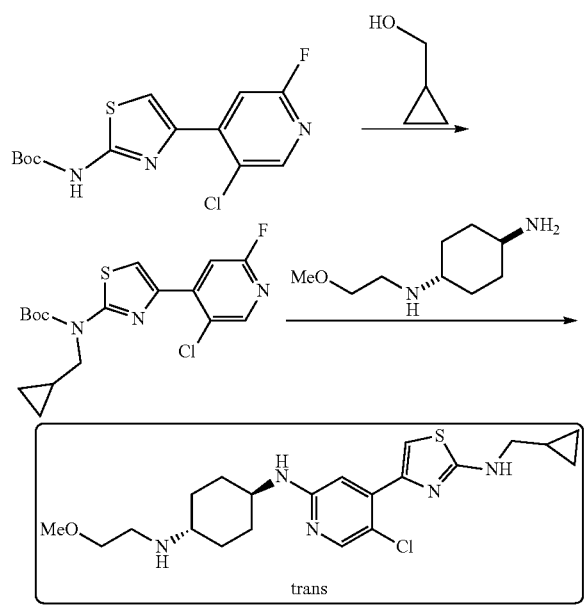

Step 1: synthesis of tert-butyl (4-(5-chloro-2-fluoropyridin-4-yl)thiazol-2-yl) (cyclopropylmethyl)carbamate Tert-butyl (4-(5-chloro-2-fluoropyridin-4-yl)thiazol-2-yl) carbamate (200 mg, 0.61 mmol) and triphenylphosphine (239 mg, 0.91 mmol) were dissolved in tetrahydrofuran (5 mL), which was replaced with nitrogen for three times, and then cyclopropylmethanol (131 mg, 1.82 mmol) was added. The mixture was stirred at room temperature for 5 minute, and then diisopropyl azodicarboxylate DIAD (184 mg, 0.91 mmol) was added. The reaction was stirred at room temperature for 2 h. TLC showed the starting material was completely consumed. The reaction solution was isolated by preparation TLC chromatograph with a developing solvent of petroleum ether/ethyl acetate=10:1 to give 230 mg of tert-butyl (4-(5-chloro-2-fluoropyridin-4-yl)thiazol-2-yl) (cyclopropylmethyl) carbamate as a yellowish white solid, yield 98%, (ESI+): m/z 384.1; [M+H]$^+$.

Step 2: synthesis of (1r, 4r)-N$^1$-(5-chloro-4-(2-((cyclopropylmethyl)amino) thiazol-4-yl)pyridin-2-yl)-N$^4$-(2-methoxyethyl)cyclohexane-1,4-diamine Tert-butyl (4-(5-chloro-2-fluoropyridin-4-yl)thiazol-2-yl) (cyclopropyl methyl)carbamate (220 mg, 0.57 mmol), (1r, 4r)-N$^1$-(2-methoxyethyl) cyclohexane-1,4-diamine (280 mg, 1.15 mmol), diisopropylethylamine DIEA (370 mg, 2.86 mol), and cesium fluoride (262 mg, 1.72 mmol) were dissolved in dimethyl sulfoxide/N,N-dimethylacetamide (3 mL/3 mL). The reaction was stirred at 120° C. for 2 days. The reaction was monitored by LCMS. When product generated, water (35 mL) was added to the reaction solution. The mixture was extracted with dichloromethane/isopropanol=3:1 (2×30 mL). The extract was washed with brine, dried over anhydrous sodium sulfate, concentrated by rotary evaporation, then mixed with silica gel and isolated by silica gel column chromatography (dichloromethane/methanol=20:1) to give a crude as yellow oil. The crude was isolated by preparation TLC chromatography with a developing solvent of dichloromethane/methanol=7:1 to give 100 mg of (1r, 4r)-N$^1$-(5-chloro-4-(2-((cyclopropylmethyl) amino)thiazol-4-yl)pyridin-2-yl)-N$^4$-(2-methoxyethyl)cyclohexane-1,4-diamine as a pale yellow solid, yield 35%, $^1$H NMR (400 MHz, DMSO) δ 7.97; (s, 1H), 7.84; (t, J=5.6 Hz, 1H), 7.28; (s, 1H), 7.04; (s, 1H), 7.74; (d, J=8.0 Hz, 2H), 3.52-3.55; (m, 3H), 3.29; (s, 3H), 3.17; (t, J=6.4 Hz, 2H), 2.94; (brs, 1H), 2.70-2.85; (m, 1H), 1.97-2.01; (m, 4H), 1.18-1.23; (m, 5H), 0.46-0.49; (m, 2H), 0.23-0.24; (m, 2H). (ESI+): m/z 436.3; [M+H]$^+$.

Example 14: Synthesis of 4-((4-(5-chloro-2-(((1r, 4r)-4-((2-methoxyethyl) amino)cyclohexyl)amino) pyridin-4-yl)thiazol-2-ylamino)methyl)tetrahydro-2H-pyran-4-carbonitrile

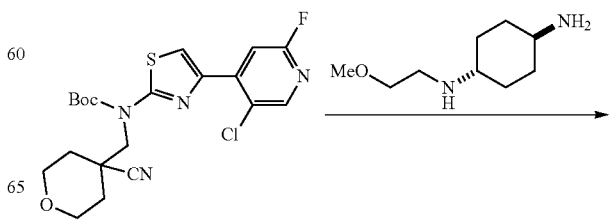

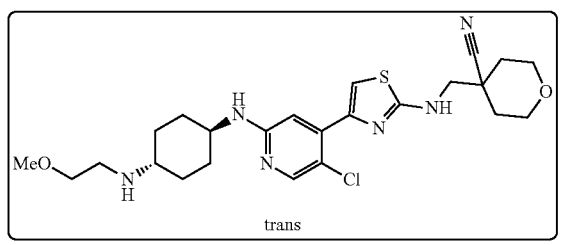

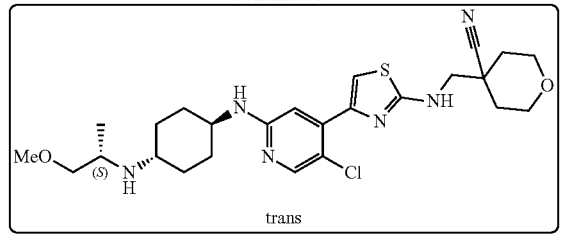

Tert-butyl (4-(5-chloro-2-fluoropyridin-4-yl)thiazol-2-yl)((4-cyano-tetrahydro-2H-pyran-4-yl)methyl)carbamate (250 mg, 0.55 mmol), (1r, 4r)-N$^1$-(2-methoxyethyl) cyclohexane-1,4-diamine (270 mg, 1.10 mmol), diisopropylethylamine DIEA (355 mg, 2.75 mol), and cesium fluoride (251 mg, 1.65 mmol) were dissolved in dimethyl sulfoxide/N,N-dimethylacetamide (3 mL/3 mL). The reaction was stirred at 120° C. for 3 days. The reaction was monitored by LCMS. When product generated, water (30 mL) was added to the reaction solution. The mixture was extracted with dichloromethane/isopropanol=3:1 (3×30 mL). The extract was dried over anhydrous sodium sulfate, concentrated by rotary evaporation, then mixed with silica gel and isolated by silica gel column chromatography (dichloromethane/methanol=10:1) to give a crude as a yellow solid. The crude was isolated by preparation TLC chromatography with a developing solvent of dichloromethane/methanol=5:1 to give 80 mg of 4-((4-(5-chloro-2-(((1r, 4r)-4-((2-methoxyethyl)amino)cyclohexyl)amino)pyridin-4-yl) thiazol-2-ylamino)methyl)tetrahydro-2H-pyran-4-carbonitrile as a pale yellow solid, yield 28%, $^1$H NMR (400 MHz, DMSO) δ 8.13; (t, J=6.0 Hz, 1H), 7.99; (s, 1H), 7.35; (s, 1H), 7.03; (s, 1H), 6.71; (d, J=7.6 Hz, 1H), 3.91-3.95; (m, 2H), 3.67; (d, J=6.4 Hz, 2H), 3.45-3.54; (m, 6H), 3.30; (s, 3H), 2.98; (brs, 2H), 2.81; (brs, 1H), 2.00-2.02; (m, 4H), 1.86-1.89; (m, 2H), 1.69-1.72; (m, 2H), 1.19-1.32; (m, 5H). (ESI+): m/z 505.3; [M+H]$^+$.

Example 15: Synthesis of 4-(((4-(5-chloro-2-(((1S,4r)-4-(((S)-1-methoxy propyl-2-yl)amino)cyclohexyl)amino)pyridin-4-yl)thiazol-2-yl)amino)methyl)tetrahydro-2H-pyran-4-carbonitrile

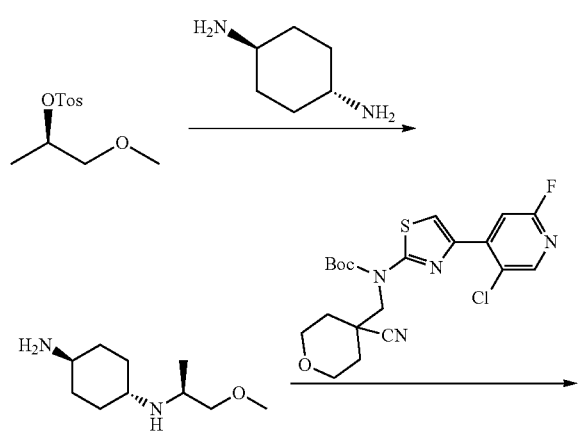

Step 1: synthesis of (1r, 4r)-N$^1$-((S)-1-methoxypropan-2-yl)cyclohexane-1,4-diamine (R)-1-methoxypropan-2-ol 4-methylbenzenesulfonate (2.0 g, 8.2 mmol) was dissolved in acetonitrile (20 mL), and trans-1,4-cyclohexanediamine (2.34 g, 20.5 mmol) was added. The reaction was stirred and refluxed at 85° C. for 16 h. TLC showed the starting material was completely consumed. The reaction solution was cooled to room temperature and filtered. The filtrate was dried by rotary evaporation, then mixed with silica gel and isolated by silica gel column chromatography (dichloromethane/methanol (containing 0.1% of a 28% aqueous ammonia solution)=10:1) to give 600 mg of (1r, 4S)-N$^1$-((S)-1-methoxy propan-2-yl)cyclohexane-1,4-diamine as yellow oil, yield 40%, (ESI+): m/z 187.2; [M+H]$^+$.

Step 2: synthesis of 4-(((4-(5-chloro-2-(((1S,4r)-4-(((S)-1-methoxypropyl-2-yl) amino)cyclohexyl)amino)pyridin-4-yl)thiazol-2-yl)amino)methyl)tetrahydro-2H-pyran-4-carbonitrile Tert-butyl (4-(5-chloro-2-fluoropyridin-4-yl)thiazol-2-yl)((4-cyano-tetra hydro-2H-pyran-4-yl)methyl)carbamate (200 mg, 0.44 mmol), (1r, 4S)-N$^1$-((S)-1-methoxypropan-2-yl)cyclohexane-1,4-diamine (200 mg, 1.08 mmol) and diisopropylethylamine DIPEA (284 mg, 2.9 mol) were dissolved in dimethyl sulfoxide (2 mL). The reaction was stirred at 130° C. for 2.5 days. The reaction was monitored by LCMS. When product generated, water (30 mL) was added to the reaction solution. The mixture was extracted with dichloromethane/isopropanol=3:1 (3×30 mL). The extract was dried over anhydrous sodium sulfate, concentrated by rotary evaporation, then mixed with silica gel and isolated by silica gel column chromatography (dichloromethane/methanol=10:1) to give a crude as a brown oil. The crude was isolated by preparation TLC chromatography with a developing solvent of dichloromethane/methanol=8:1 to give 50 mg of 4-(((4-(5-chloro-2-(((1S,4r)-4-(((S)-1-methoxypropyl-2-yl)amino)cyclohexyl)amino)pyridin-4-yl)thiazol-2-yl)amino) methyl)tetrahydro-2H-pyran-4-carbonitrile as pale yellow solid, yield 22%, $^1$H NMR (400 MHz, DMSO) δ 8.12; (t, J=6.0 Hz, 1H), 7.98; (s, 1H), 7.35; (s, 1H), 7.03; (s, 1H), 6.69; (d, J=8.0 Hz, 1H), 3.91-3.95; (m, 2H), 3.66; (d, J=6.4 Hz, 2H), 3.55-3.65; (m, 1H), 3.47-3.51; (m, 3H), 3.29; (s, 3H), 3.17; (d, J=4.8 Hz, 1H), 1.86-1.99; (m, 6H), 1.66-1.74; (m, 2H), 0.99-1.26; (m, 8H). (ESI+): m/z 519.3; [M+H]$^+$.

Example 16: Synthesis of (1r, 4r)-N¹-(5-chloro-4-(2-((tetrahydro-2H-pyran-4-yl)methoxy)thiazol-4-yl)pyridin-2-yl)-N⁴-(2-methoxyethyl)cyclohexane-1,4-diamine

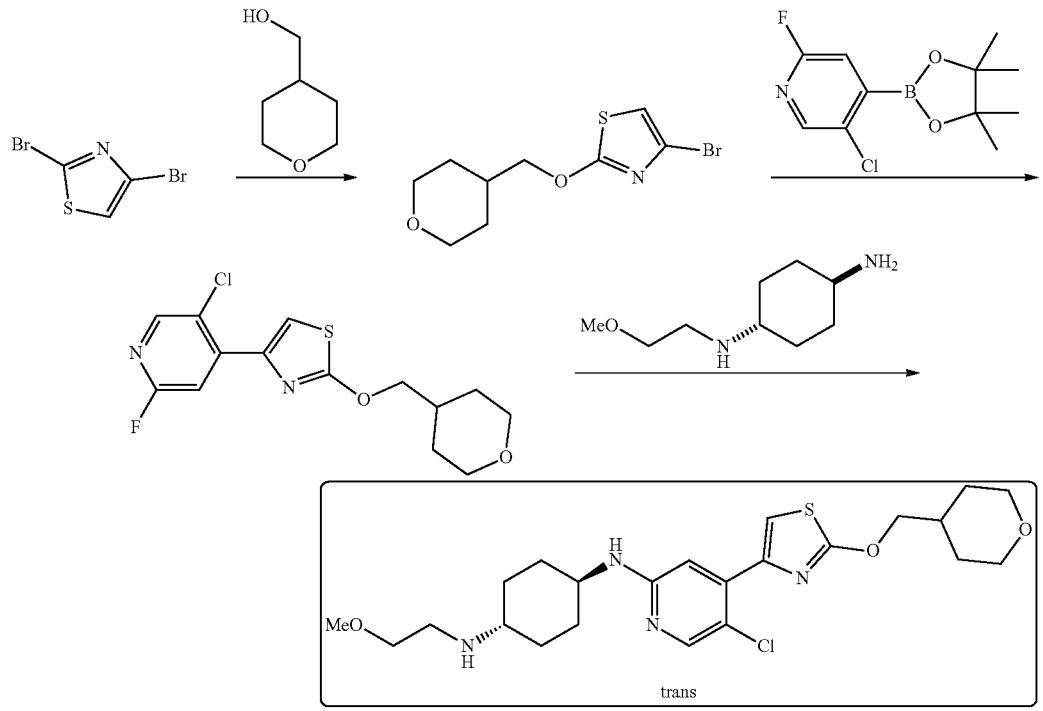

Step 1: synthesis of 4-bromo-2-((tetrahydro-2H-pyran-4-yl)methoxy) thiazole (Tetrahydro-2H-pyran-4-yl)methanol (5.0 g, 20.8 mmol) was dissolved in 50 mL of tetrahydrofuran (50 mL) and then NaH (996 mg, 24.9 mmol) was added. The mixture was stirred for 10 minutes at room temperature and then 2,4-dibromothiazole (5.0 g, 20.8 mmol) was added. Then the mixture was stirred at room temperature overnight. After 100 ml of a saturated ammonium chloride solution was added to the reaction solution, the mixture was extracted with ethyl acetate twice, 50 ml each time. The organic phases were then combined, dried over anhydrous sodium sulfate, and then concentrated by rotary evaporation. The residue was isolated by column chromatography (petroleum ether: ethyl acetate=100:1) to give 4.2 g of 4-bromo-2-((tetrahydro-2H-pyran-4-yl)methoxy)thiazole as a white solid. yield 73%. (ESI+): m/z 278.0; [M+H]⁺.

Step 2: synthesis of 4-(5-chloro-2-fluoropyridin-4-yl)-2-((tetrahydro-2H-pyran-4-yl)methoxy)thiazole 4-bromo-2-((tetrahydro-2H-pyran-4-yl)methoxy)thiazole (2.0 g, 7.22 mmol) and 5-chloro-2-fluoro-4-(4,4,5,5-tetramethyl-1,3,2-dioxaborolan-2-yl)pyridine (3.71 g, 14.44 mmol) were added to a mixed solvent of 20 ml of dioxane and 4 ml of water and Pd(dppf)Cl₂ (161 mg, 0.22 mmol) and Na₂CO₃ (2.3 g, 21.66 mmol) were further added. Being protected under nitrogen, the mixture was heated to 80° C., and stirred overnight. After 50 ml of water was added to the reaction solution, the mixture was extracted with ethyl acetate twice, 50 ml each time. The organic phases were then combined, dried over anhydrous sodium sulfate, and then concentrated by rotary evaporation. The residue was isolated by column chromatography (petroleum ether: ethyl acetate=30:1) to give 1.45 g of 4-(5-chloro-2-fluoropyridin-4-yl)-2-((tetrahydro-2H-pyran-4-yl)methoxy)thiazole as a white solid. yield 61.2%. (ESI+): m/z 329.1; [M+H]⁺.

Step 3: synthesis of (1r, 4r)-N¹-(5-chloro-4-(2-((tetrahydro-2H-pyran-4-yl) methoxy)thiazol-4-yl)pyridin-2-yl)-N⁴-(2-methoxyethyl)cyclohexane-1,4-diamine 4-(5-chloro-2-fluoropyridin-4-yl)-2-((tetrahydro-2H-pyran-4-yl)methoxy)thiazole (300 mg, 0.915 mmol), (1r, 4r-N¹-(2-methoxyethyl)cyclohexane-1,4-diamine (245 mg, 1.006 mmol) and K₂CO₃ (104 mg, 2.745 mmol) were added to 5 mL of DMSO. Then the mixture was heated to 100° C. with stirring and reacted for 48 hours. The reaction was monitored by LCMS and most of the starting materials were completely reacted. The reaction solution was cooled to room temperature and then 50 mL of water was added. Then the mixture was extracted with ethyl acetate twice, 10 ml each time. The organic phases were combined, dried over anhydrous sodium sulfate, and then concentrated by rotary evaporation. The obtained crude product was isolated by column chromatography (dichloromethane:methanol=20:1). Finally 111.0 mg of (1r, 4r)-N¹-(5-chloro-4-(2-((tetrahydro-2H-pyran-4-yl)methoxy)thiazol-4-yl)pyridin-2-yl)-N⁴-(2-methoxyethyl)cyclohexane-1,4-diamine was obtained as a pale brown solid. yield 25.3%. ¹H NMR (400 MHz, CDCl₃) δ 8.07; (s, 1H), 7.50; (s, 1H), 6.95; (s, 1H), 4.39; (d, J=8.0 Hz, 1H), 4.31; (d, J=6.4 Hz, 2H), 4.03; (dd, J1=3.2 Hz, J2=11.2 Hz, 2H), 3.59-3.61; (m, 1H), 3.54; (t, J=4.8 Hz, 2H), 3.44-3.47; (m, 2H), 3.37; (s, 3H), 2.85; (t, J=5.2 Hz, 2H), 2.53-2.54; (m, 1H), 2.15-2.18; (m, 3H), 2.00-2.03; (m, 2H), 1.73-1.76; (m, 2H), 1.46-1.52; (m, 2H), 1.15-1.37; (m, 5H). (ESI+): m/z 481.2; [M+H]⁺.

Example 17: synthesis of (1r, 4r)-N$^1$-(5-chloro-4-(2-(((tetrahydro-2H-pyran-4-yl)methyl)mercapto)thiazol-4-yl)pyridin-2-yl)-N$^4$-(2-methoxyethyl)cyclohexane-1,4-diamine

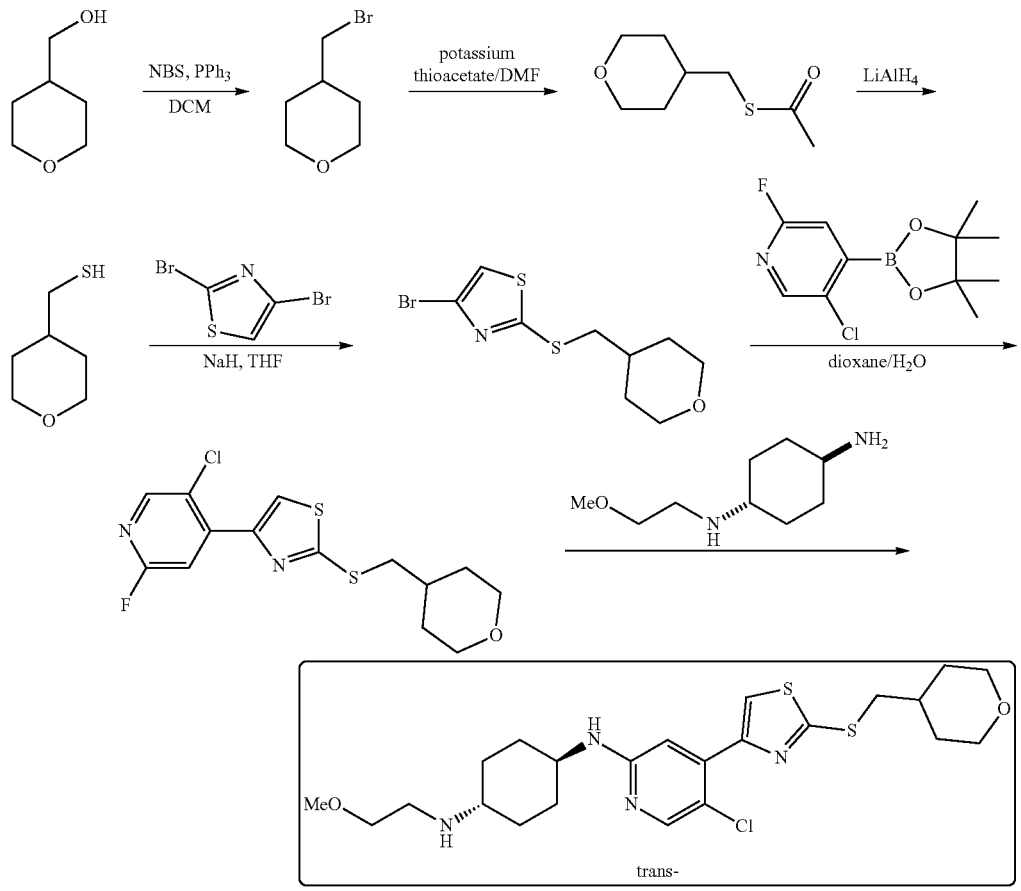

Step 1: synthesis of 4-(bromomethyl)-tetrahydro-2H-pyran (Tetrahydro-2H-pyran-4-yl)methanol (8.12 g, 10 mmol) and N-bromosuccinimide NBS (13.71 g, 2448 mmol) were added to 400 mL of dichloromethane, which was cooled to 0° C., and then triphenylphosphorus was slowly added in portions. The reaction was stirred at room temperature for 1-2 hours and TLC showed the disappearance of the starting materials. The reaction solution was poured into water (100 mL). The mixture was extracted with dichloromethane. The organic phase was washed with saturated brine, dried over sodium sulfate, and isolated by column chromatography (petroleum ether/ethyl acetate=20/1) to give 6.2 g of 4-(bromomethyl)-tetrahydro-2H-pyran as a colorless liquid, yield 49%, (ESI+): m/z 179.0; [M+H]$^+$.

Step 2: synthesis of methyl S-(tetrahydro-2H-pyran-4-yl) thioacetate 4-(bromomethyl)-tetrahydro-2H-pyran and potassium thioacetate were added to 60 mL of DMF. The mixture was warmed up to 90° C. and reacted for 2 hours. When TLC showed the starting materials disappeared, the heating was stopped, and the reaction was treated. The reaction solution was cooled to room temperature, and poured into ice water. The mixture was extracted with ethyl acetate (3×30 mL). The organic phase was washed with saturated brine, dried over anhydrous sodium sulfate, and filtered. The filtrate was mixed with silica gel and isolated by column (petroleum ether/ethyl acetate=30/1, 20:1, 10:1) to give 1.8 g of methyl S-(tetrahydro-2H-pyran-4-yl) thioacetate as yellow oil, yield 69%. (ESI+): m/z 175.1; [M+H]$^+$.

Step 3: synthesis of (tetrahydro-2H-pyran-4-yl)methyl mercaptan

Methyl S-(tetrahydro-2H-pyran-4-yl) thioacetate was add to THF, which was protected under nitrogen and cooled to 0° C., lithium aluminum hydride was slowly added in batches, and reacted overnight. The reaction was monitored by TLC. The reaction solution was diluted with tetrahydrofuran (50 mL) and an appropriate amount of sodium sulfate decahydrate was slowly added in batches. The mixture was stirred for 10 min, filtered, and concentrated to give 0.68 g of a crude product (tetrahydro-2H-pyran-4-yl)methyl mercaptan as yellow oil, yield 100%. (ESI+): m/z 133.1; [M+H]$^+$.

Step 4: synthesis of 4-bromo-2-(((tetrahydro-2H-pyran-4-yl)methyl)sulfydryl) thiazole (Tetrahydro-2H-pyran-4-yl)methyl mercaptan (0.632 g, 4.8 mmol) was dissolved in tetrahydrofuranTHF, which was protected under nitrogen and cooled to 0° C., and then sodium hydride NaH (0.2 g, 4.8 mmol) was slowly added in batches, and reacted at room temperature for 10 min. A solution of 2,4-dibromothiazole in 30 mL of tetrahydrofuran THF was added dropwise and reacted overnight. When TLC showed that the reaction was almost completed, the reaction was stopped. The reaction solution was poured into saturated ammonium chloride and quenched. The mixture was extracted with ethyl acetate (3×30 mL). The organic phases were combined, dried over anhydrous sodium sulfate, filtered, and concentrated to give a crude as yellowish brown oil. The crude was isolated by column chromatography (petroleum ether/ethyl acetate=25:1, 20:1) to give 0.7 g of 4-bromo-2-(((tetrahydro-2H-pyran-4-yl)methyl) sulfydryl) thiazole as an off-white solid, yield 60%. (ESI+): m/z 294.0; [M+H]$^+$.

Step 5: synthesis of 4-(5-chloro-2-fluoropyridin-4-yl)-2-(((tetrahydro-2H-pyran-4-yl)methyl)sulfydryl) thiazole 4-bromo-2-(((tetrahydro-2H-pyran-4-yl)methyl)sulfydryl)thiazole (0.45 g, 1.512 mmol), 5-chloro-2-fluoro-4-(4,4,5,5-tetramethyl-1,3,2-dioxaborolan-2-yl) pyridine (0.788 g, 3.0 mmol), tetrakistriphenylphosphine palladium Pd(PPh$_3$)$_4$ (0.18 g, 0.151 mmol) and sodium carbonate (0.405 g, 3.78 mmol) were added to 20 mL of dioxane and 4 mL of water, which was protected under nitrogen, then warmed up to 90° C. and reacted overnight. The reaction was monitored by TLC and LCMS. When the starting materials were disappeared completely, the reaction was stopped. The reaction solution was cooled and then water (80 mL) was added. The mixture was extracted with ethyl acetate (3×30 mL). The organic phases were combined, dried over anhydrous sodium sulfate, filtered, and concentrated to give a crude as a yellowish brown oil. The crude was isolated by chromatography (petroleum ether/ethyl acetate=30:1, 25:1) to give 0.27 g of 4-(5-chloro-2-fluoropyridin-4-yl)-2-(((tetrahydro-2H-pyran-4-yl)methyl)sulfydryl)thiazole as yellow oil, yield 42%. (ESI+): m/z 345.0; [M+H]$^+$.

Step 6: synthesis of (1r, 4r)-N$^1$-(5-chloro-4-(2-(((tetrahydro-2H-pyran-4-yl)methyl)mercapto)thiazol-4-yl)pyridin-2-yl)-N$^4$-(2-methoxyethyl)cyclohexane-1,4-diamine 4-(5-Chloro-2-fluoropyridin-4-yl)-2-(((tetrahydro-2H-pyran-4-yl)methyl)sulfydryl)t thiazole (0.27 g, 0.756 mmol), (1r, 4r)-N$^1$-(2-methoxyethyl)cyclohexane-1,4-diamine (0.203 g, 0.831 mmol) and K$_2$CO$_3$ (0.313 g, 2.268 mmol) were added to DMSO, which was protected under nitrogen, and then warmed up to 100° C. and reacted for two days. The reaction was monitored by TLC and LCMS. The starting material of 4-(5-chloro-2-fluoropyridin-4-yl)-2-(((tetrahydro-2H-pyran-4-yl)methyl)sulfydryl)thiazole remained and the reaction was stopped. The reaction mixture was cooled and diluted with ethyl acetate (20 mL), water (800 mL) was added under ice bath, and separated. The aqueous phase was then extracted with ethyl acetate (2×20 mL). The organic phases were combined, dried over anhydrous sodium sulfate, filtered, and concentrated to give a crude as yellowish brown oil. The crude was isolated by chromatography (dichloromethane/methanol=15:1) to give 0.135 g of (1r, 4r)-N$^1$-(5-chloro-4-(2-(((tetrahydro-2H-pyran-4-yl)methyl)sulfydryl)thiazol-4-yl)pyridin-2-yl)-N$^4$-(2-methoxyethyl)cyclohexane-1,4-diamine as a yellow solid, yield 34.5%. $^1$H NMR (400 MHz, CDCl$_3$) δ 8.07; (s, 1H), 7.98; (s, 1H), 6.99; (s, 1H), 4.42; (brs, 1H), 3.91-4.10; (m, 2H), 3.55-3.71; (m, 3H), 2.83-3.52; (m, 12H), 2.13-2.17; (m, 4H), 1.95-2.05; (m, 1H), 1.69-1.87; (m, 2H), 1.31-1.56; (m, 5H), 1.02-1.35; (m, 4H), 0.79-0.95; (m, 1H). (ESI+): m/z 497.2; [M+H]$^+$.

Example 18: Synthesis of (1r, 4r)-N$^1$-(2-methoxyethyl)-N$^4$-(4-(2-(((tetrahydro-2H-pyran-4-yl)methyl)amino)thiazol-4-yl)pyridin-2-yl)cyclohexane-1,4-diamine

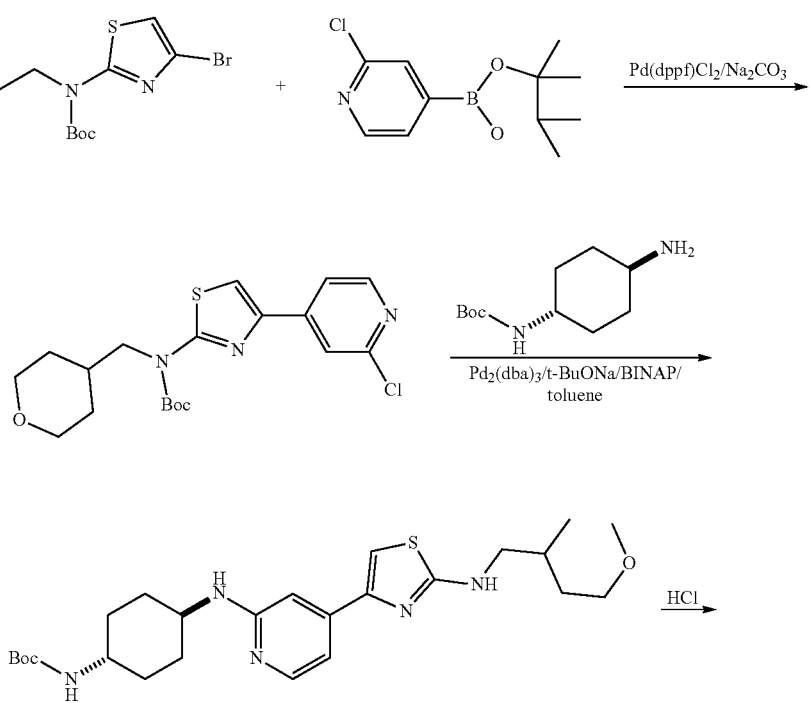

-continued

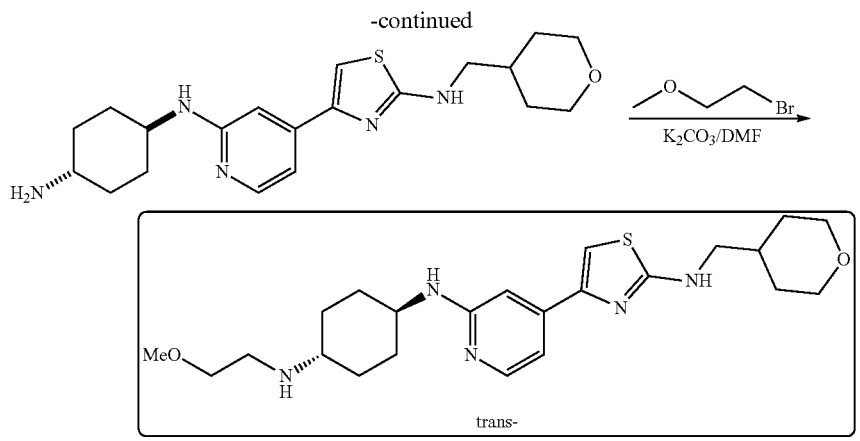

Step 1: synthesis of tert-butyl (4-(2-chloropyridin-4-yl)thiazol-2-yl) ((tetrahydro-2H-pyran-4-yl)methyl)carbamate Tert-butyl (4-bromothiazol-2-yl)((tetrahydro-2H-pyran-4-yl)methyl) carbamate (1 g, 1.512 mmol), 2-chloro-4-(4,4,5,5-tetramethyl-1,3,2-dioxaborolan-2-yl)pyridine (0.95 g, 3.0 mmol), Pd(dppf)Cl$_2$ (0.22 g, 0.151 mmol) and Na$_2$CO$_3$ (0.703 g, 3.78 mmol) were added to 15 mL of dioxane and 30 mL of water, which was protected under nitrogen, then warmed up to 80° C. and reacted overnight. The reaction was monitored by TLC and LCMS. When the starting materials were disappeared completely, the reaction was stopped. The reaction solution was cooled and then water (50 mL) was added. The mixture was extracted with ethyl acetate (3×30 mL). The organic phases were combined, dried over anhydrous sodium sulfate, filtered, and concentrated to give a crude as a yellowish brown oil. The crude was isolated by chromatography (petroleum ether/ethyl acetate=30:1) to give 0.27 g of tert-butyl (4-(2-chloropyridin-4-yl)thiazol-2-yl) ((tetrahydro-2H-pyran-4-yl)methyl) carbamate as yellow oil, yield 42%. (ESI+): m/z 410.1; [M+H]$^+$.

Step 2: synthesis of ((1r, 4r)-4-((4-(2-(((tetrahydro-2H-pyran-4-yl)methyl) amino)thiazol-4-yl)pyridin-2-yl)amino)cyclohexyl)carbamate Tert-butyl (4-(2-chloropyridin-4-yl)thiazol-2-yl)((tetrahydro-2H-pyran-4-yl) methyl)carbamate (0.388 g, 0.95 mmol), tert-butyl ((1r, 4r)-4-aminocyclohexyl) carbamate (0.244 g, 1.14 mmol), Pd$_2$(dba)$_3$ (0.026 g, 3.8 mmol), sodium tert-butoxide, (±)-2,2'-bis-(diphenylphosphino)-1,1'-binaphthyl BINAP (0.035 g, 0.0285 mmol) were added to toluene, which was protected under nitrogen and then warmed up to 120° C. and reacted overnight. The reaction was monitored by TLC. When the starting materials were disappeared completely, the reaction was stopped. The reaction solution was cooled and poured into a saturated aqueous solution of ammonium chloride (20 mL) and separated. The aqueous phase was then extracted with ethyl acetate (2×20 mL). The organic phases were combined, dried over anhydrous sodium sulfate, filtered, and concentrated to give 600 mg of ((1r, 4r)-4-((4-(2-(((tetrahydro-2H-pyran-4-yl)methyl)amino) thiazol-4-yl)pyridin-2-yl)amino)cyclohexyl) carbamate as yellowish brown oil. The crude product was directly used in the next step, and the yield was calculated in the next step. (ESI+): m/z 488.3; [M+H]$^+$.

Step 3: Synthesis of (1r, 4r)-N$^1$-(4-(2-(((tetrahydro-2H-pyran-4-yl)methyl) amino)thiazol-4-yl)pyridin-2-yl)cyclohexane-1,4-diamine Tert-butyl ((1r, 4r)-4-((4-(2-(((tetrahydro-2H-pyran-4-yl) methyl)amino)thiazol-4-yl)pyridin-2-yl)amino)cyclohexyl) carbamate (0.6 g, 0.95 mmol) was added to methanol and 5 mL of hydrochloric acid (6N) was added and reacted overnight. Then the reaction solution was concentrated, and saturated sodium bicarbonate solution was added to adjust pH=7. The aqueous phase was then extracted with ethyl acetate (2×20 mL) and concentrated. The residue was soaked overnight with dichloromethane:methanol=10:1, and filtered. The filtrate was concentrated to give 0.12 g of (1r, 4r)-N$^1$-(4-(2-(((tetrahydro-2H-pyran-4-yl)methyl)amino) thiazol-4-yl)pyridin-2-yl)cyclohexane-1,4-diamine as pale yellow oil, yield: 31% (2 steps). (ESI+): m/z 388.2; [M+H]$^+$.

Step 4: synthesis of (1r, 4r)-N$^1$-(2-methoxyethyl)-N$^4$-(4-(2-(((tetrahydro-2H-pyran-4-yl)methyl)amino) thiazol-4-yl)pyridin-2-yl)cyclohexane-1,4-diamine (1r, 4r)-N$^1$-(4-(2-(((tetrahydro-2H-pyran-4-yl)methyl) amino)thiazol-4-yl) pyridin-2-yl)cyclohexane-1,4-diamine (0.66 g, 1.7 mmol), 2-bromoethyl methyl ether (0.240 g, 1.7 mmol) and potassium carbonate (0.235 g, 1.7 mmol) were added to N,N dimethylformamide, which was protected under nitrogen, and then warmed up to 100° C. and reacted for two days. The reaction was monitored by TLC and LCMS. Although the starting materials remained a few, the reaction was stopped. The reaction solution was cooled and then water (30 mL) was added. The mixture was extracted with ethyl acetate (3×20 mL). The organic phases were combined, dried over anhydrous sodium sulfate, filtered, and concentrated to give a crude as a yellowish brown oil. The crude was isolated by thick preparation plate (dichloromethane/methanol=8:1) to give 0.057 g of (1r,4r)-N$^1$-(2-methoxyethyl)-N$^4$-(4-(2-(((tetrahydro-2H-pyran-4-yl) methyl)amino)thiazol-4-yl)pyridin-2-yl)cyclohexane-1,4-diamine as yellow oil, yield 15%. $^1$H NMR (400 MHz, CDCl$_3$) δ 7.95-8.02; (m, 1H), 6.79-6.89; (m, 3H), 5.48; (brs, 1H), 4.65-4.85; (m, 1H), 3.98-4.01; (m, 2H), 3.57-3.61; (m, 3H), 3.35-3.42; (m, 5H), 3.18-3.20; (m, 2H), 2.89-2.92; (m, 2H), 2.61-2.68; (m, 1H), 2.17-2.27; (m, 3H), 2.04-2.08; (m, 3H), 1.87-1.96; (m, 1H), 1.69-1.73; (m, 2H), 1.20-1.50; (m, 10H), 0.79-0.95; (m, 2H). (ESI+): m/z 446.3; [M+H]$^+$.

Example 19: Effect of CDK9 Inhibitors on Cancer Cell Growth

By testing the effect of CDK9 inhibitors on cancer cell growth, we evaluated the selectivity of compounds for inhibiting cancer cell proliferation.

In the examples, we used acute myelocytic leukemia (AML) OCI-AML-3, acute promyelocytic leukemia cell line NB-4, MDS-RAEB (myelodysplastic syndrome-excess blasts type) cell line SKM-1, human leukemia cell Nomo-1, acute myeloid leukemia cell line MOLM14, acute myeloid leukemia cell line MOLM13, acute myeloid leukemia cell line MV4-11, acute myeloid leukemia cell line HL-60, acute myeloid leukemia cell line OCI-AML-2, histiocytic lymphoma U-937, acute B cell leukemia cell line MEC-1, acute B cell leukemia cell line MEC-2, acute megakaryoblastic leukemia CMK, hamster lung cell CHL, hamster ovary cell CHO, human non-small cell lung cancer cell H1975, human non-small cell lung cancer cell H358, human small cell lung cancer cell H209, human lung adenocarcinoma cell H1395, human non-small cell lung cancer cell PC-9, human lung cancer cell H3122, human non-small cell lung cancer cell H2122, human non-small cell lung cancer cell H1915, human lung adenocarcinoma cell H1355, human non-small cell lung cancer cell HCC827, human breast cancer cell MDA-MB-231, human breast cancer cell MDA-MB-468, human breast cancer cell MCF-7, human breast cancer cell T47D, human breast cancer cell SK-Br-3, the above cells were purchased from ATCC. In addition, Palbociclib (a CDK4/6 selective inhibitor purchased from Shanghai Haoyuan Chemical), HY-16462 (CDK9-IN-2, purchased from Shanghai Haoyuan) and Dinaciclib (a CDK1/2/5/9 inhibitor, purchased from Shanghai Haoyuan Chemical) were used as control compounds.

In the examples, the compounds of the present invention with different concentrations (0.000508 μM, 0.00152 μM, 0.00457 μM, 0.0137 μM, 0.0411 μM, 0.123 μM, 0.370 μM, 1.11 μM, 3.33 μM, 10 μM) and the control compounds were separately added to the above cells which were incubated for 72 hours. Cell Titer-Glo® (Promega, USA) chemical self-luminescence cell viability assay kit was used to detect the number of viable cells by quantitatively measuring ATP in living cells, according to which to calculate $GI_{50}$ and $IC_{50}$. The results were shown in tables 1-3: tables 1 and 2 showed $GI_{50}$ of the compounds of the invention against the blood system disease cell lines tested; table 3 showed $IC_{50}$ of compound 1 against cells of cancer type other than hematological cancer.

Based on the results of tables 1 and 2, the compounds of the present invention tested were found to have strong inhibitory effects on cancer cells tested, such as leukemia cells and lymphoma cells, and compound 1 and 14 also showed good selectivity: it had no inhibitory effect on normal cell CHL and CHO cells, while the reference drug Dinaciclib and HY-16462 had certain inhibitory effects on CHL and CHO. The results in table 3 also showed that compound 1 of the present invention also exhibited significant inhibitory effects on human non-small cell lung cancer cells, human small cell lung cancer cells, lung adenocarcinoma cells, and breast cancer cells, whereas Palbociclib had no obvious inhibition on cancer cells tested. These results provided an important theoretical basis for the use of compound 1 as a less toxic selective CDK9 kinase inhibitor for the treatment of these cancers.

TABLE 1

| Compound No. | CHO | CHL | CMK | HL-60 | MOLM-13 | MOLM-14 | MV4-11 | NB4 |
|---|---|---|---|---|---|---|---|---|
| 1 | 1.6 | 1.1 | 0.049 | 0.032 | 0.025 | 0.025 | 0.014 | 0.035 |
| 2 | 2.8 | 3.5 | 0.37 | 0.55 | 0.15 | 0.14 | 0.14 | 0.056 |
| 5 | 1.2 | 3.6 | 1.5 | 0.39 | 0.64 | 0.49 | 0.44 | 0.46 |
| 6 | 0.4 | 1.1 | 0.35 | 0.065 | 0.13 | 0.11 | 0.14 | 0.11 |
| 8 | 1.6 | 0.93 | 0.15 | 0.31 | 0.2 | 0.53 | 0.55 | 0.22 |
| 9 | 1.2 | 1.9 | 1.8 | 0.42 | 1 | 0.68 | 0.53 | 0.7 |
| 10 | 0.78 | 8 | 0.98 | 0.41 | 0.82 | 0.33 | 1.1 | 0.49 |
| 11 | 0.37 | 1 | 0.47 | 0.073 | 0.28 | 0.16 | 0.33 | 0.27 |
| 12 | 0.47 | 1.1 | 0.72 | 0.19 | 0.29 | 0.31 | 0.88 | 0.41 |
| 13 | 0.77 | 1.4 | 1.1 | 0.32 | 0.44 | 0.33 | 0.74 | 0.34 |
| 14 | 1.1 | 1.2 | 0.036 | 0.056 | 0.012 | 0.0011 | 0.041 | 0.0079 |
| 16 | 1.3 | 3.3 | 1.4 | 0.45 | 0.57 | 0.62 | 0.63 | 0.58 |
| 17 | 0.61 | 5.6 | 1.1 | 0.16 | 0.34 | 0.36 | 1.1 | 0.35 |
| 18 | 4.1 | 1.2 | 4 | 0.98 | 1.2 | 1.2 | 0.91 | 1.3 |
| HY-16462 | 0.29 | 0.2 | 0.042 | 0.037 | 0.032 | 0.033 | 0.027 | 0.032 |
| Dinaciclib | 0.16 | 0.18 | 0.0099 | 0.008 | 0.0033 | 0.0045 | 0.0076 | 0.01 |

TABLE 2

| Compound No. | Nomo-1 | OCI-AML2 | OCI-AML3 | SKM-1 | U-937 | MEC-1 | MEC-2 |
|---|---|---|---|---|---|---|---|
| 1 | 0.045 | 0.033 | 0.033 | 0.033 | 0.017 | 0.047 | 0.025 |
| 2 | 0.59 | 9.1 | 0.14 | 0.085 | 0.12 | 0.27 | 0.14 |
| 5 | 1 | 0.47 | 0.82 | 0.35 | 0.43 | 1.3 | 0.77 |
| 6 | 0.29 | 0.12 | 0.15 | 0.097 | 0.11 | 0.31 | 0.13 |
| 8 | 1 | 2.9 | 0.72 | 0.15 | 1.4 | 3.6 | 0.83 |
| 9 | 1.3 | 0.65 | 1.1 | 0.75 | 0.85 | 1.4 | 1.1 |
| 10 | 0.6 | 0.6 | 0.56 | 0.33 | 0.34 | 0.85 | 0.66 |
| 11 | 0.96 | 0.33 | 0.22 | 0.17 | 0.22 | 0.47 | 0.32 |
| 12 | 0.92 | 0.41 | 0.39 | 0.2 | 0.39 | 0.45 | 0.48 |
| 13 | 0.87 | 0.6 | 0.42 | 0.26 | 0.32 | 0.89 | 0.66 |

TABLE 2-continued

| Compound No. | Nomo-1 | OCI-AML2 | OCI-AML3 | SKM-1 | U-937 | MEC-1 | MEC-2 |
|---|---|---|---|---|---|---|---|
| 14 | 0.11 | 0.0066 | 0.012 | 0.002 | 0.011 | 0.037 | 0.023 |
| 16 | 1.5 | 2.1 | 0.63 | 0.5 | 0.6 | 1.4 | 0.97 |
| 17 | 0.93 | 0.8 | 0.98 | 0.33 | 0.3 | 0.8 | 0.7 |
| 18 | 3 | 1.1 | 2.1 | 1.1 | 1.1 | 2.5 | 1.7 |
| HY-16462 | 0.063 | 0.071 | 0.047 | 0.04 | 0.031 | 0.048 | 0.036 |
| Dinaciclib | 0.034 | 0.013 | 0.011 | 0.01 | 0.0036 | 0.011 | 0.01 |

TABLE 3

| $IC_{50}$ (μM) | Compound 1 | Palbociclib | Dinaciclib |
|---|---|---|---|
| H358 | 0.043 | 6.6 | 0.043 |
| H209 | 0.086 | >10 | 0.077 |
| H1395 | 0.12 | >10 | 0.056 |
| H3122 | 0.011 | 1.2 | 0.011 |
| PC-9 | 0.09 | >10 | 0.013 |
| H1975 | 0.042 | >10 | 0.029 |
| H2122 | 0.049 | 1.6 | 0.039 |
| H1915 | 0.037 | 3.6 | 0.023 |
| H1355 | 0.1 | ~10 | 0.025 |
| HCC827 | 0.06 | >10 | 0.028 |
| MDA-MB-231 | 0.074 | 5.1 | 0.063 |
| MDA-MB-468 | 0.018 | 2.7 | 0.013 |
| MCF-7 | 0.006 | 1.7 | 0.0082 |
| T47D | 0.055 | 4.1 | 0.054 |
| SK-Br-3 | 0.04 | 3.2 | 0.015 |

Example 20: Enzyme Assay for Inhibition of CDK Protein In Vitro

Compounds 1 and 14 diluted in DMSO were mixed with detected CDK protein (Invitrogen, USA) respectively, incubated at room temperature for 30 minutes; and then mixed with Kinase/Z-LYTE™ Peptide Substrate Mixture (Invitrogen, USA) and 4×ATP. The mixed system was transferred to a 384-well white opaque plate to react for 1 hour at room temperature; 5 μL of Development Solution (Invitrogen, USA) was added to react at room temperature for 1 hour, and finally Stop Reagent (Invitrogen, USA) was added to terminate the reaction and MD SpectraMax I3× microplate reader (Molecular Devices, USA) was used to read fluorescence values. The $IC_{50}$ values of Compounds 1 and 14 against the tested CDK protein were calculated based on the read fluorescence values using Prism 5.0 (GraphPad Software, San Diego, Calif.) and shown in table 4 below.

TABLE 4

| $IC_{50}$(nM) | Compound 1 | Compound 14 |
|---|---|---|
| CDK1/cyclin B | 5410 | 1340 |
| CDK2/cyclin A | 6850 | 2860 |
| CDK3/cyclin E1 | >10,000 | >10,000 |
| CDK5/p25 | 6950 | 4640 |
| CDK7/cyclin HMNAT1 | 3700 | 1720 |
| CDK8/cyclin C | >10,000 | >10,000 |
| CDK9/cyclin T1 | 0.928 | 1.27 |
| CDK11(non-active) | >10,000 | >10,000 |
| CDK14/cyclin Y | 2710 | 1680 |
| CDK16/cyclin Y | 195 | 292 |

Example 21: Effect of CDK9 Inhibitors on Signaling Pathway

Against four cells, acute myelocytic leukemia cell line (AML) OCI-AML-3, acute promyelocytic leukemia cell line NB-4, acute myelocytic leukemia cell line (AML) HL-60 and acute myelocytic leukemia cell line (AML) MV4-11 (all purchased from ATCC), by measuring the biochemical endpoints and functional endpoints of multiple cells, the effect of compound 1 was evaluated on CDK9 in cells and other protein kinases related to its signaling pathway, such as RNAPII, XIAP, MCL-1, c-MYC, BCL-2 and so on. Compound 1 (in DMSO) in different concentrations of 0 μM, 0.03 μM, 0.1 μM, 0.3 μM, 1 μM and 3 μM, and the reference drugs Dinaciclib and HY-16462 (CDK9-IN-2) (purchased from Shanghai Haoyuan) (in DMSO) in 1 μM were used to treat these cell lines for 2 hours and then samples were collected. The effect of Compound 1 on the phosphorylation of CDK9, RNAPII, XIAP, MCL-1, c-MYC, BCL-2 in these cell lines was determined (FIG. 1a-d).

In the four cell lines, acute myelocytic leukemia cell line (AML) OCI-AML-3, acute promyelocytic leukemia cell line NB-4, acute myelocytic leukemia cell line (AML) HL-60 and acute myelocytic leukemia cell line (AML) MV4-11, compound 1 was found to have a significant inhibitory effect on the phosphorylation of RNAPII, MCL-1, and c-MYC directly downstream of CDK9 protein.

Example 22: Effect of Novel Kinase Inhibitors on Apoptosis

In order to prove whether the cell death is through apoptosis or necrosis, in the four cell lines, acute myelocytic leukemia cell line (AML) OCI-AML-3, acute promyelocytic leukemia cell line NB-4, acute myelocytic leukemia cell line (AML) HL-60 and acute myelocytic leukemia cell line (AML) MV4-11 (all purchased from ATCC), the effect of compound 1 on DNA repair enzyme polyadenosine diphosphate-ribose polymerase PARP closely related to apoptosis and protein shear of cysteine-containing aspartate proteolytic enzyme Caspase 3 were detected in cells. Compound 1 (in DMSO) in different concentrations of 0 μM, 0.01 μM, 0.03 μM and 0.1 μM, Dinaciclib (in DMSO) in 0.01 μM, and HY-16462 (in DMSO) in 0.1 μM were used to treat different cells and then the cells were collected after 24 hours. Western Blot was used to detect the effects of drugs in different concentrations on DNA repair enzyme polyadenylation diphosphate-ribose polymerase PARP and protein shear of cysteine-containing aspartate proteolytic enzyme Caspase 3 at different time intervals.

The experimental results were shown in FIGS. 2a-d: in the four cell lines, acute myelocytic leukemia cell line (AML) OCI-AML-3, acute promyelocytic leukemia cell line NB-4, acute myelocytic leukemia cell line (AML) HL-60 and acute myelocytic leukemia cell line (AML) MV4-11, it was obviously found that there was shear of partially DNA repair enzyme polyadenylation diphosphate-ribose polymerase PARP or downstream Caspase 3 of PARP. This demonstrated that compound 1 could cause apoptosis in the four cells, acute myelocytic leukemia cell line (AML) OCI-AML-3, acute promyelocytic leukemia cell line NB-4, acute myelocytic leukemia cell line (AML) HL-60, and acute myelocytic leukemia cell line (AML) MV4-11.

Example 23: Effect of Novel Kinase Inhibitors on Cell Cycle

In order to study in which cycle the cells were prevented after administration, in the three cell lines, acute promyelocytic leukemia cell line NB-4, acute myelocytic leukemia cell line (AML) HL-60, and acute myelocytic leukemia cell line (AML) MV4-11, the effects of compound 1 on the cell cycle distribution of these cell lines were tested. Compound 1 in different concentrations of 0 μM, 0.01 μM, 0.03 μM and 0.1 μM (in DMSO), CDK9 kinase inhibitor Dinaciclib in 0.01 μM (in DMSO) and HY-16462 in 0.1 μM (in DMSO) were used to treat HL-60, MV4-11 or NB-4 cell lines for 12 hours, 24 hours, or 48 hours, and then the cells were collected, washed twice with 1×PBS buffer, fixed by 75% ethanol at −20° C. for 24 hours, and then washed twice with 1×PBS buffer. 0.5 mL of 1×PBS buffer and 0.5 mL of PI staining solution (purchased from BD Bioscience, USA) were added to the cells and the cells were placed in the dark at 37° C. for 15 miniutes for staining. The cell cycle distribution was measured by flow cytometry (BD FACS Calibur). The results were shown in FIGS. 3a-c.

Figure 1A:
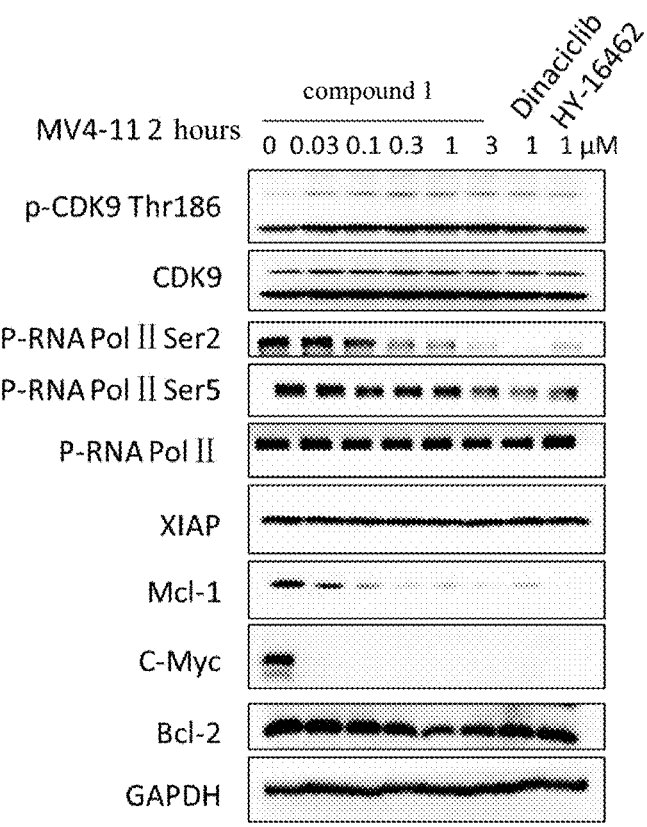
FIGS. 1a-1d show the effects of compound 1 on cellular signaling pathways in MV4-11 (FIG. 1a), OCI-AML-3 (FIG. 1b), HL-60 (FIG. 1c) and NB4 (FIG. 1d) cell lines.
Figure 1B:
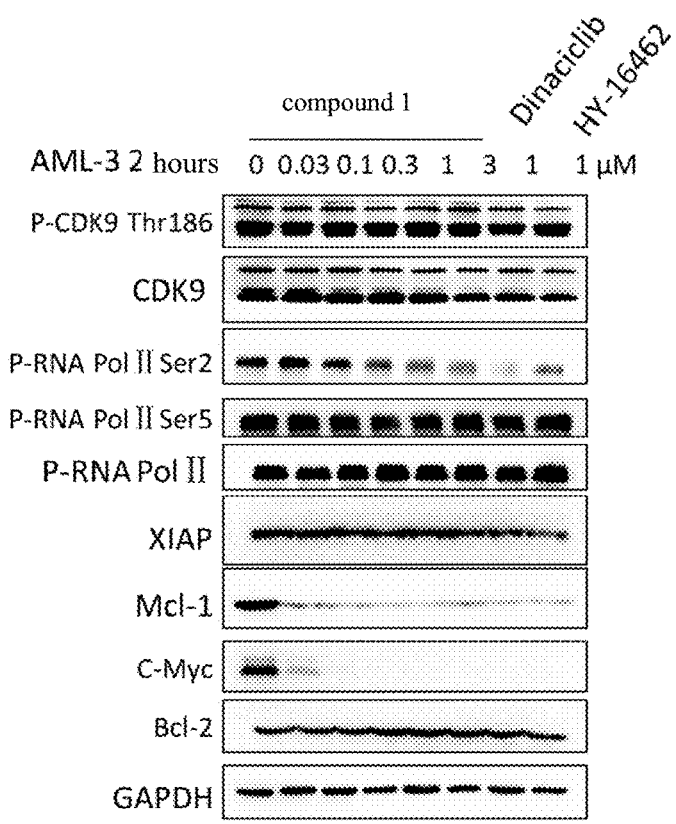
Figure 1C:
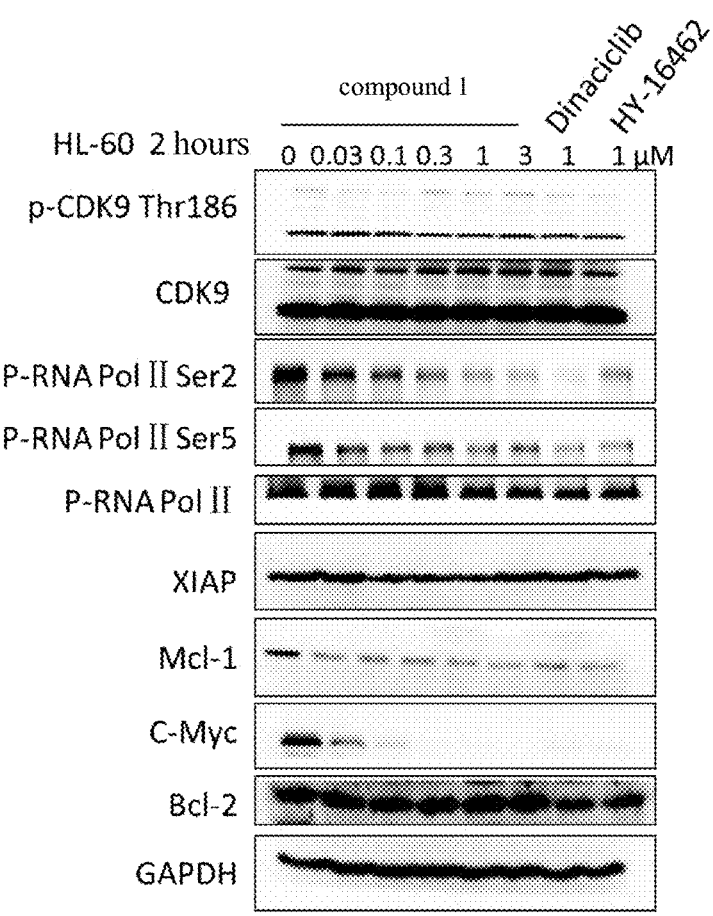
Figure 1D:
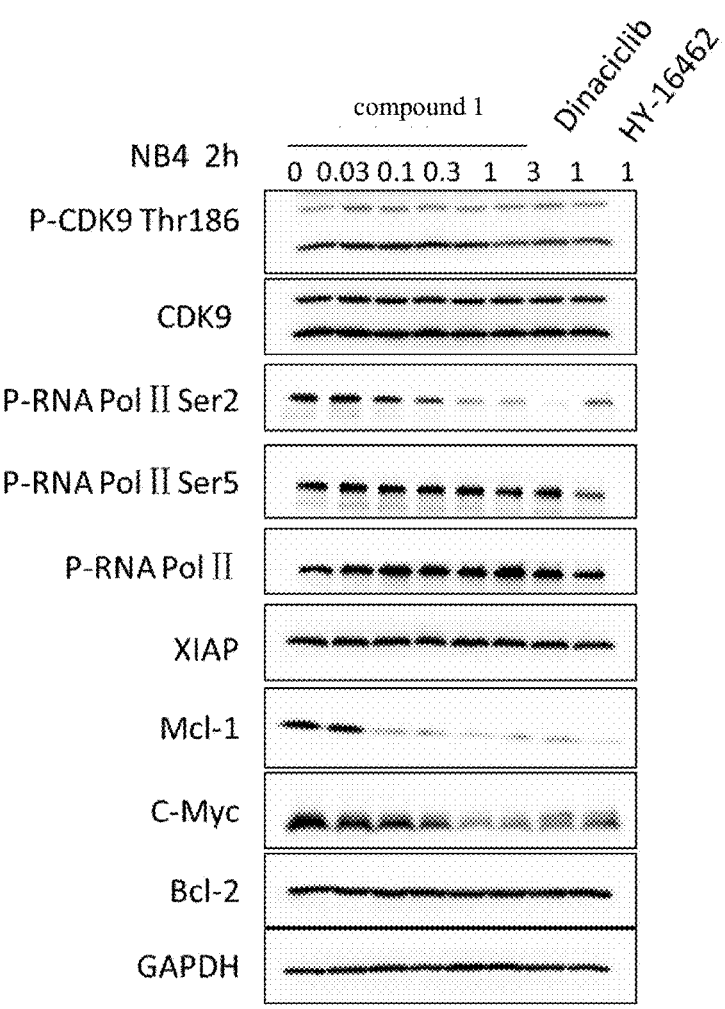
Figure 2A:
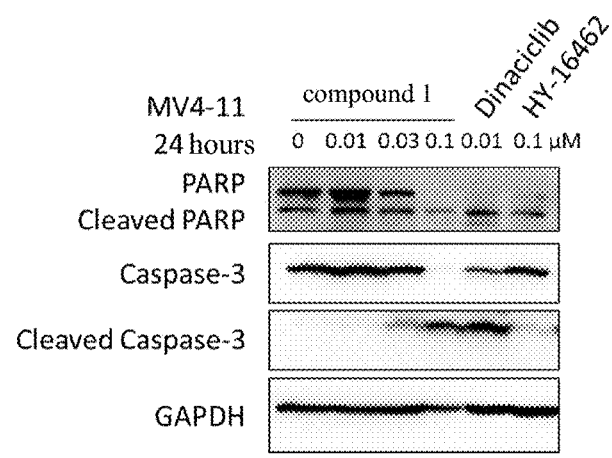
FIGS. 2a-2d show the effects of compound 1 on apoptosis-related proteins in MV4-11 (FIG. 2a), OCI-AML-3 (FIG. 2b), HL-60 (FIG. 2c) and NB4 (FIG. 2d) cell lines.
Figure 2B:
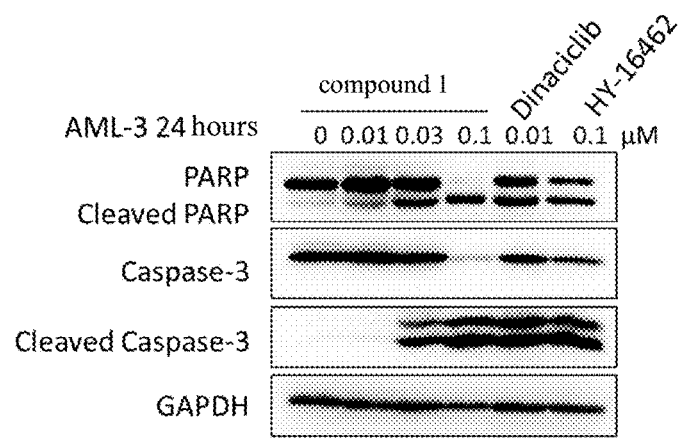
Figure 2C:
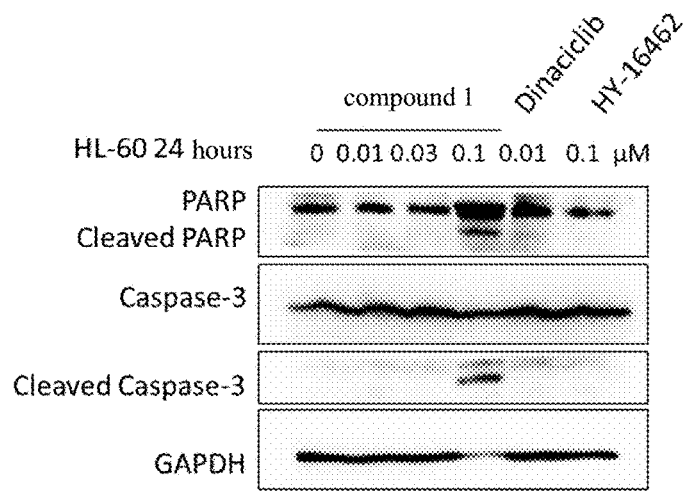
Figure 2D:
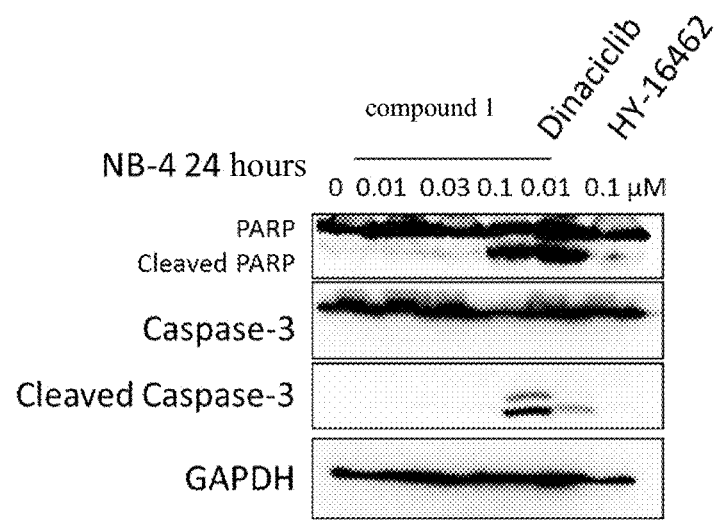
Figure 3A:
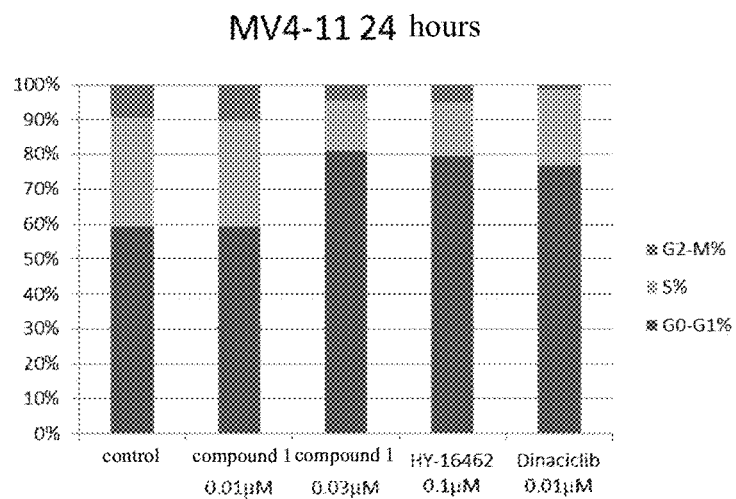
FIGS. 3a-3c show the effects of compound 1 on cell cycle in MV4-11 (FIG. 3a), HL-60 (FIG. 3b) and NB4 (FIG. 3c) cell lines.
Figure 3B:
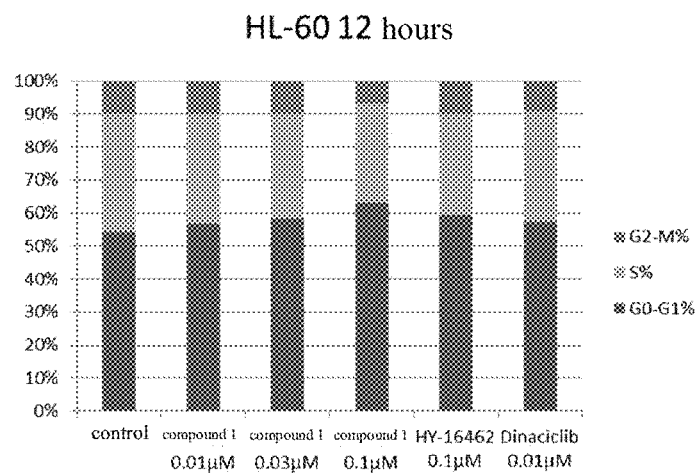
Figure 3C:
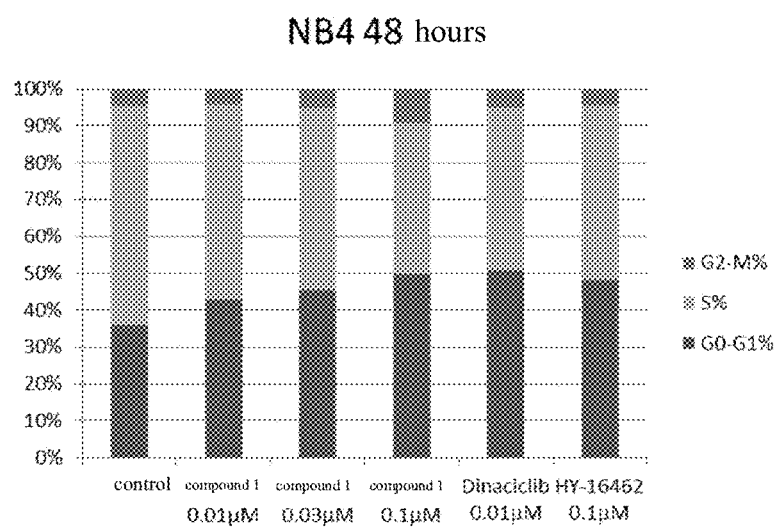

The results were shown in FIGS. 3a-c: after the three cell lines, acute myelocytic leukemia cell line (AML) HL-60, acute myelocytic leukemia cell line (AML) MV4-11 and acute promyelocytic leukemia cell line NB-4, were treated for 12 hours, 24 hours or 48 hours respectively, it was found that compound 1 had an effect on the cell cycle of these three cells, that is, compound 1 blocked the cells in G0-G1 phase.

Example 24: Experimental Results of Compound 1 in Human Acute Granulocyte Leukemia MV4-11 Mouse Model 24 Bal b/c female mice, 4-6 weeks, were purchased from Shanghai Slack Laboratory Animals Co., Ltd. and kept in SPF laboratory. The drinking water and padding were aseptically treated by autoclaving. All operations were carried out under aseptic conditions. On day 0, 5×10$^6$MV4-11 acute granulocyte leukemia cells (purchased from ATCC) were subcutaneously injected into the left side of all mice' back. Starting on day 15, all mice were divided into four groups (6 mice per group), methyl cellulose (HKI) solvent was orally administered to the first group of mice per day; compound 1 at a dose of 10 mg/kg mice body weight was orally administered to the second group of mice per day; compound 1 at a dose of 20 mg/kg mice body weight was orally administered to the third group of mice per day; compound 1 at a dose of 30 mg/kg mice body weight was orally administered to the fourth group of mice per day. From the start of administration, the length/width of the subcutaneous tumor was measured with a vernier caliper every day, and the body weight of the mouse was recorded every day, and the effect of compound 1 on the body weight of the mouse was observed. On day 43, the mice were sacrificed, subcutaneous tumors were taken out, and tumors were weighed and compared, and then a sample of protein lysate was prepared from the tumor sample tissue for use. The trend of subcutaneous tumor growth was counted within day 16 to day 43, and the tumor volume was calculated as: length×width×width/2 mm$^3$.

The experiment results were shown in the figure. The results showed that for the inhibitor compound 1 disclosed in the present invention, the high dose group (20, 30 mg/kg) affected the body weight of Bal b/c mice, but in the low dose group (10 mg/kg), the weight of the subcutaneous tumor had been significantly reduced and there was no significant effect on the body weight of the mice; the tumor growth inhibition (TGI) of the high dose group (20, 30 mg/kg) could reach 98.7%. This indicated that compound 1 was effective in inhibiting the growth of subcutaneous tumors (FIG. 4a-c).

INDUSTRIAL APPLICABILITY

The present invention provides an inhibitor of cyclin-dependent kinase CDK9 which can be used in the treatment, prevention or amelioration of a disease, disorder, or condition regulated or affected by serine kinase activity, or related to cyclin-dependent kinase activity. Thus, it can be made into a corresponding drug suitable for industrial applications.

Although the present invention has been described in detail herein, the present invention is not limited thereto, and those skilled in the art can make modifications in accordance with the principles of the present invention. Therefore, various modifications in accordance with the principles of the present invention should be understood as falling within the scope of the present invention.

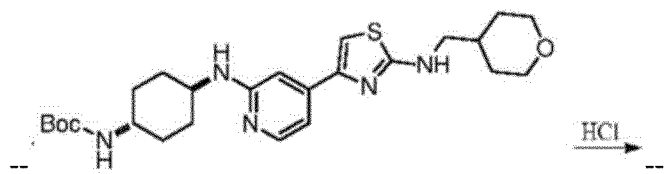

What is claimed:
1. A compound of formula (I):

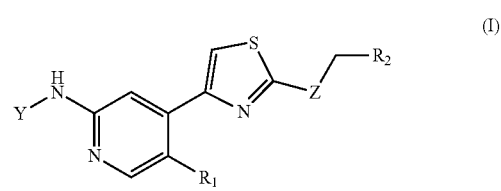

or a pharmaceutically acceptable salt, solvate, ester, acid or prodrug thereof,
wherein Y is selected from the group consisting of p-fluorobenzoyl, trans-4-aminocyclohexyl in which N is optionally substituted with $R_3$, and trans-4-aminocyclohexylmethyl in which N is optionally substituted with $R_3$;
Z is selected from the group consisting of NH, S and O;
$R_1$ is selected from the group consisting of hydrogen and halogen;
$R_2$ is selected from the group consisting of hydrogen, C1-C3 alkyl, C3-C6 cycloalkyl, C3-C6 heterocycloalkyl optionally substituted with $R_4$, and phenyl optionally substituted with $R_4$;
$R_3$ is selected from the group consisting of C2-C6 alkanoyl and C1-C3 alkoxy (C1-C3) alkyl;
$R_4$ is selected from the group consisting of cyano and halogen.

2. The compound or a pharmaceutically acceptable salt, solvate, ester, acid or prodrug thereof according to claim 1, wherein $R_1$ is chlorine.

3. The compound or a pharmaceutically acceptable salt, solvate, ester, acid or prodrug thereof according to claim 1, wherein $R_2$ is selected from the group consisting of hydrogen, methyl, cyclopropyl, cyclohexyl, 4-tetrahydropyranyl optionally substituted with cyano, and phenyl optionally substituted with fluorine.

4. The compound or a pharmaceutically acceptable salt, solvate, ester, acid or prodrug thereof according to claim 1, wherein R₃ is selected from the group consisting of acetyl, 2-methoxyethyl, (R)-1-methyl-2-methoxyethyl, and (S)-1-methyl-2-methoxyethyl.

5. The compound or a pharmaceutically acceptable salt, solvate, ester, acid or prodrug thereof according to claim 1, wherein the compound is selected from:
- 4-(((4-(5-chloro-2-(((1R,4r)-4-(((R)-1-methoxypropyl-2-yl)amino)cyclohexyl)amino)pyridin-4-yl)thiazol-2-yl)amino)methyl)tetrahydro-2H-pyran-4-carbonitrile;
- (1r,4r)-N¹-(5-chloro-4-(2-(((tetrahydro-2H-pyran-4-yl)methyl)amino)thiazol-4-yl)pyridin-2-yl)cyclohexane-1,4-diamine;
- N-((1r,4r)-4-((5-chloro-4-(2-(((tetrahydro-2H-pyran-4-yl)methyl)amino)thiazol-4-yl)pyridin-2-yl)amino)cyclohexyl)acetamide;
- (1r,4r)-N¹-(5-chloro-4-(2-(((tetrahydro-2H-pyran-4-yl)methyl)amino)thiazol-4-yl)pyridin-2-yl)-N⁴-(2-methoxyethyl)cyclohexyl-1,4-diamine;
- (1 S,4r)-N¹-(5-chloro-4-(2-(((tetrahydro-2H-pyran-4-yl)methyl)amino)thiazol-4-yl)pyridin-2-yl)-N⁴-((S)-1-methoxypropan-2-yl)cyclohexyl-1,4- diamine;
- (1R,4r)-N¹-(5-chloro-4-(2-(((tetrahydro-2H-pyran-4-yl)methyl)amino)thiazol-4-yl)pyridin-2-yl)-N⁴-((R)-1-methoxypropan-2-yl)cyclohexane-1,4- diamine;
- 4-(2-((((1r,4r)-4-aminocyclohexyl)methyl)amino)-5-chloropyridin-4-yl)-N-((tetrahydro-2H-pyran-4-yl)methyl)thiazol-2-amine;
- N-(5-chloro-4-(2-(((tetrahydro-2H-pyran-4-yl)methyl)amino)thiazol-4-yl)pyridin-2-yl)-4-fluorobenzamide;
- (1r,4r)-N¹-(5-chloro-4-(2-(methylamino)thiazol-4-yl)pyridin-2-yl)-N⁴-(2-methoxyethyl)cyclohexane-1,4-diamine;
- (1r,4r)-N¹-(5-chloro-4-(2-((cyclohexylmethyl)amino)thiazol-4-yl)pyridin-2-yl)-N⁴-(2-methoxyethyl)cyclohexane-1,4-diamine;
- (1r,4r)-N¹-(4-(2-(benzylamino)thiazol-4-yl)-5-chloropyridin-2-yl)-N⁴-(2-methoxyethyl)cyclohexane-1,4-diamine;
- (1r,4r)-N¹-(5-chloro-4-(2-((4-fluorobenzyl)amino)thiazol-4-yl)pyridin-2-yl)-N⁴-(2-methoxyethyl)cyclohexane-1,4-diamine;
- (1r,4r)-N¹-(5-chloro-4-(2-((cyclopropylmethyl)amino)thiazol-4-yl)pyridin-2-yl)-N⁴-(2-methoxyethyl)cyclohexane-1,4-diamine;
- 4-((4-(5-chloro-2-(((1r,4r)-4-((2-methoxyethyl)amino)cyclohexyl)amino)pyridin-4-yl)thiazol-2-ylamino)methyl)tetrahydro-2H-pyran-4-carbonitrile;
- 4-(((4-(5-chloro-2-(((1S,4r)-4-(((S)-1-methoxypropyl-2-yl)amino)cyclohexyl)amino)pyridin-4-yl)thiazol-2-yl)amino)methyl)tetrahydro-2H-pyran-4-carbonitrile;
- (1r,4r)-N¹-(5-chloro-4-(2-((tetrahydro-2H-pyran-4-yl)methoxy)thiazol-4-yl)pyridin-2-yl)-N⁴-(2-methoxyethyl)cyclohexane-1,4-diamine;
- (1r,4r)-N¹-(5-chloro-4-(2-(((tetrahydro-2H-pyran-4-yl)methyl)mercapto)thiazol-4-yl)pyridin-2-yl)-N⁴-(2-methoxyethyl)cyclohexane-1,4-diamine; and
- (1r,4r)-N¹-(2-methoxyethyl)-N⁴-(4-(2-(((tetrahydro-2H-pyran-4-yl)methyl)amino)thiazol-4-yl)pyridin-2-yl)cyclohexane-1,4-diamine.

6. A pharmaceutical composition comprising the compound or a pharmaceutically acceptable salt, solvate, ester, acid or prodrug thereof according to claim 1, and a pharmaceutically acceptable carrier or excipient, and optional other therapeutic agents.

7. A method of treating or ameliorating a disease, disorder or condition regulated or effected by serine kinase activity or related to cyclin-dependent kinase activity in a subject, wherein the method comprises administering the subject with the compound or a pharmaceutically acceptable salt, solvate, ester, acid or prodrug thereof according to claim 1.

8. The method of claim 7, wherein the disease, disorder or condition is cancer.

9. The method of claim 8, the cancer is selected from the group consisting of non-small cell lung cancer, small cell lung cancer, lung adenocarcinoma, lung squamous carcinoma, pancreatic cancer, prostate cancer, bladder cancer, liver cancer, skin cancer, glioma, breast cancer, melanoma, malignant glioma, rhabdomyosarcoma, ovarian cancer, astrocytoma, Ewing's sarcoma, retinoblastoma, epithelial cell carcinoma, colon cancer, renal cancer, gastrointestinal stromal tumor, leukemia, histiocytic lymphoma, and nasopharyngeal carcinoma.

10. The method of claim 7, wherein the disease, disorder or condition is selected from the group consisting of MDS-RAEB (myelodysplastic syndrome-excess blasts type), histiocytic lymphoma, acute B cell leukemia, acute megakaryoblastic leukemia, acute myeloid leukemia, and acute promyelocytic leukemia.

* * * * *

UNITED STATES PATENT AND TRADEMARK OFFICE
CERTIFICATE OF CORRECTION

PATENT NO. : 10,952,999 B2
APPLICATION NO. : 16/606136
DATED : March 23, 2021
INVENTOR(S) : Gang Zhou It is certified that error appears in the above-identified patent and that said Letters Patent is hereby corrected as shown below:

In the Specification

Column 6, Lines 7-12:

" 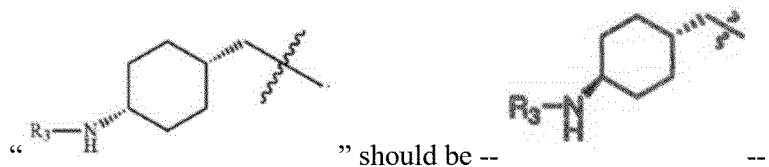 " should be -- --

Column 9, Lines 2-9, the structure of compound 12 should be:

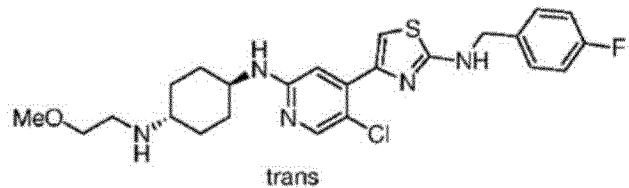

-- --

Column 9, Lines 47-53, the structure of compound 17 should be:

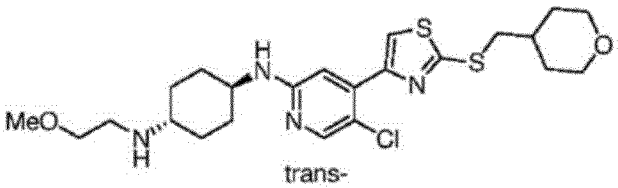

-- --

Column 17, Lines 34-36:
"(1r,4r)-M-(5-chloro-4-(2-(((tetrahydro-2H-pyran-4-yl)methyl)amino)thiazol-4-yl)pyridin-2-yl)cyclohexane-1,4-diamine"

Signed and Sealed this
Twenty-fourth Day of May, 2022

Katherine Kelly Vidal
*Director of the United States Patent and Trademark Office*

CERTIFICATE OF CORRECTION (continued)
U.S. Pat. No. 10,952,999 B2

Should be:
--(1r,4r)-N$^1$-(5-chloro-4-(2-(((tetrahydro-2H-pyran-4-yl)methyl)amino)thiazol-4-yl)pyridin-2-yl)cyclohexane-1,4-diamine--

Column 27, Lines 1-3:
"(1r,4r)-N$^1$-(5-chloro-4-(2-(methylamino)thiazol-4-yl)pyridin-2-yl)-M-(2-methoxyethyl)cyclohexane-1,4-diamine"

Should be:
--(1r,4r)-N$^1$-(5-chloro-4-(2-(methylamino)thiazol-4-yl)pyridin-2-yl)-N$^4$-(2-methoxyethyl)cyclohexane-1,4-diamine--

Column 42, Lines 59-67, should be: